United States Patent
Ivosevic et al.

(10) Patent No.: US 10,052,259 B2
(45) Date of Patent: Aug. 21, 2018

(54) SEAL SYSTEM FOR CANNULA

(71) Applicant: Becton Dickinson and Company LTD., Dun Laoghaire (IE)

(72) Inventors: Milan Ivosevic, Kinnelon, NJ (US); Erik Witt, Wyckoff, NJ (US); Paul Paia Marici, Piscataway, NJ (US); Brandon W. Craft, Reisterstown, MD (US)

(73) Assignee: Becton Dickinson and Company LTD., Dun Laoghaire (IE)

( * ) Notice: Subject to any disclaimer, the term of this patent is extended or adjusted under 35 U.S.C. 154(b) by 98 days.

(21) Appl. No.: 15/206,842

(22) Filed: Jul. 11, 2016

(65) Prior Publication Data
US 2016/0317389 A1 Nov. 3, 2016

Related U.S. Application Data

(63) Continuation of application No. 14/204,383, filed on Mar. 11, 2014, now Pat. No. 9,414,990.
(Continued)

(51) Int. Cl.
*A61J 1/20* (2006.01)
*A61J 1/14* (2006.01)
(Continued)

(52) U.S. Cl.
CPC .......... *A61J 1/2096* (2013.01); *A61J 1/1406* (2013.01); *A61J 1/1425* (2015.05); *A61J 1/201* (2015.05);
(Continued)

(58) Field of Classification Search
CPC .......... A61J 1/2096; A61J 1/2082; A61J 1/22; A61J 1/2048; A61J 1/1425; A61J 1/201;
(Continued)

(56) References Cited

U.S. PATENT DOCUMENTS 2,541,272 A * 2/1951 Murphy .............. A61M 5/1782
141/285
3,332,421 A * 7/1967 King ..................... A61J 1/2089
141/25
(Continued)

FOREIGN PATENT DOCUMENTS

EP 2462971 A1 6/2012
JP 60501294 A 8/1985
(Continued)

*Primary Examiner* — Nicolas A Arnett
(74) *Attorney, Agent, or Firm* — The Webb Law Firm

(57) ABSTRACT

A system includes a needle hub having a proximal end and a distal end. The proximal end of the needle hub has a connection portion configured to receive a first container. The system further includes a cannula received by the needle hub with the cannula having a proximal end and a distal end and a cannula seal having a resilient sleeve enclosing at least a portion of the cannula. The system also includes a vial adapter configured to be attached to a second container with the vial adapter having a vial seal that is configured to engage the cannula seal. The cannula seal has a first position where the cannula seal encloses the distal end of the cannula and a second position where the cannula seal is retracted to expose the distal end of the cannula.

22 Claims, 23 Drawing Sheets

Related U.S. Application Data

(60) Provisional application No. 61/787,674, filed on Mar. 15, 2013.

(51) Int. Cl.
*A61J 1/22* (2006.01)
*A61M 5/32* (2006.01)

(52) U.S. Cl.
CPC .......... *A61J 1/2048* (2015.05); *A61J 1/2082* (2015.05); *A61J 1/22* (2013.01); *A61M 5/3293* (2013.01); *A61J 1/2072* (2015.05); *A61M 2005/3258* (2013.01)

(58) Field of Classification Search
CPC .... A61J 1/1406; A61J 1/2072; A61M 5/3293; A61M 2005/3258
USPC .............................. 141/18, 25, 27, 319–320
See application file for complete search history.

(56) References Cited

U.S. PATENT DOCUMENTS

| | | | |
|---|---|---|---|
| 3,872,867 A | 3/1975 | Killinger | |
| 4,564,054 A | 1/1986 | Gustavsson | |
| 4,673,404 A | 6/1987 | Gustavsson | |
| 4,917,672 A | 4/1990 | Terndrup et al. | |
| 4,932,937 A | 6/1990 | Gustavsson et al. | |
| 5,088,996 A | 2/1992 | Kopfer et al. | |
| 5,122,129 A | 6/1992 | Olson et al. | |
| 5,135,510 A | 8/1992 | Maszkiewicz et al. | |
| 5,280,876 A | 1/1994 | Atkins | |
| 5,290,254 A | 3/1994 | Vaillancourt | |
| 5,334,188 A | 8/1994 | Inoue et al. | |
| 5,360,011 A | 11/1994 | McCallister | |
| 5,395,348 A | 3/1995 | Ryan | |
| 5,437,650 A | 8/1995 | Larkin et al. | |
| 5,464,123 A | 11/1995 | Scarrow | |
| 5,472,430 A | 12/1995 | Vaillancourt et al. | |
| 5,478,324 A | 12/1995 | Meyer | |
| 5,478,328 A * | 12/1995 | Silverman | A61M 5/32 604/110 |
| 5,487,728 A | 1/1996 | Vaillancourt | |
| 5,507,733 A | 4/1996 | Larkin et al. | |
| 5,509,911 A | 4/1996 | Cottone, Sr. et al. | |
| 5,545,152 A | 8/1996 | Funderburk et al. | |
| 5,607,392 A | 3/1997 | Kanner | |
| 5,609,584 A | 3/1997 | Gettig et al. | |
| 5,611,792 A | 3/1997 | Gustafsson | |
| 5,641,010 A | 6/1997 | Maier | |
| 5,647,845 A | 7/1997 | Haber et al. | |
| 5,685,866 A | 11/1997 | Lopez | |
| 5,807,347 A | 9/1998 | Bonaldo | |
| 5,897,526 A | 4/1999 | Vaillancourt | |
| 6,063,068 A | 5/2000 | Fowles et al. | |
| 6,089,541 A | 7/2000 | Weinheimer et al. | |
| 6,113,583 A | 9/2000 | Fowles et al. | |
| 6,132,404 A | 10/2000 | Lopez | |
| 6,221,041 B1 | 4/2001 | Russo | |
| 6,221,056 B1 | 4/2001 | Silverman | |
| 6,343,629 B1 | 2/2002 | Wessman et al. | |
| 6,409,708 B1 | 6/2002 | Wessman | |
| 6,478,788 B1 | 11/2002 | Aneas | |
| 6,524,278 B1 | 2/2003 | Campbell et al. | |
| 6,551,299 B2 | 4/2003 | Miyoshi et al. | |
| 6,585,695 B1 | 7/2003 | Adair et al. | |
| 6,599,273 B1 | 7/2003 | Lopez | |
| 6,610,040 B1 | 8/2003 | Fowles et al. | |
| 6,629,958 B1 | 10/2003 | Spinello | |
| 6,656,433 B2 | 12/2003 | Sasso | |
| 6,715,520 B2 | 4/2004 | Andreasson et al. | |
| 6,729,370 B2 | 5/2004 | Norton et al. | |
| 6,814,726 B1 | 11/2004 | Lauer | |
| 6,852,103 B2 | 2/2005 | Fowles et al. | |
| 6,875,203 B1 | 4/2005 | Fowles et al. | |
| 6,875,205 B2 | 4/2005 | Leinsing | |
| 6,911,025 B2 | 6/2005 | Miyahara | |
| 7,040,598 B2 | 5/2006 | Raybuck | |
| 7,083,605 B2 | 8/2006 | Miyahara | |
| 7,097,209 B2 | 8/2006 | Unger et al. | |
| 7,306,584 B2 | 12/2007 | Wessman et al. | |
| 7,350,535 B2 | 4/2008 | Liepold et al. | |
| 7,354,427 B2 | 4/2008 | Fangrow | |
| 7,452,349 B2 | 11/2008 | Miyahara | |
| 7,547,300 B2 | 6/2009 | Fangrow | |
| 7,628,772 B2 | 12/2009 | McConnell et al. | |
| 7,648,491 B2 | 1/2010 | Rogers | |
| 7,658,734 B2 | 2/2010 | Adair et al. | |
| 7,743,799 B2 | 6/2010 | Mosler et al. | |
| 7,744,581 B2 | 6/2010 | Wallen et al. | |
| 7,758,560 B2 | 7/2010 | Connell et al. | |
| 7,803,140 B2 | 9/2010 | Fangrow, Jr. | |
| 7,867,215 B2 | 1/2011 | Akerlund et al. | |
| 7,879,018 B2 | 2/2011 | Zinger et al. | |
| 7,900,659 B2 | 3/2011 | Whitley et al. | |
| 7,927,316 B2 | 4/2011 | Proulx et al. | |
| 7,942,860 B2 | 5/2011 | Horppu | |
| 7,975,733 B2 | 7/2011 | Horppu et al. | |
| 8,096,525 B2 | 1/2012 | Ryan | |
| 8,122,923 B2 | 2/2012 | Kraus et al. | |
| 8,123,738 B2 | 2/2012 | Vaillancourt | |
| 8,177,768 B2 | 5/2012 | Leinsing | |
| 8,206,367 B2 | 6/2012 | Warren et al. | |
| 8,211,069 B2 | 7/2012 | Fangrow, Jr. | |
| 8,226,628 B2 | 7/2012 | Muramatsu et al. | |
| 8,257,286 B2 | 9/2012 | Meyer et al. | |
| 8,267,127 B2 | 9/2012 | Kriheli | |
| 8,277,424 B2 | 10/2012 | Pan | |
| 8,317,743 B2 | 11/2012 | Denenburg | |
| 8,398,607 B2 | 3/2013 | Fangrow, Jr. | |
| 8,403,905 B2 | 3/2013 | Yow | |
| 8,425,487 B2 | 4/2013 | Beiriger et al. | |
| 8,454,579 B2 | 6/2013 | Fangrow, Jr. | |
| 9,414,990 B2 * | 8/2016 | Ivosevic | A61J 1/2096 |
| 9,597,260 B2 * | 3/2017 | Ivosevic | A61J 1/2096 |
| 2003/0070726 A1 | 4/2003 | Andreasson et al. | |
| 2004/0112457 A1 | 6/2004 | Norton et al. | |
| 2005/0065495 A1 | 3/2005 | Zambaux | |
| 2005/0182383 A1 | 8/2005 | Wallen | |
| 2005/0215976 A1 | 9/2005 | Wallen | |
| 2006/0118749 A1 | 6/2006 | Ryan et al. | |
| 2007/0079894 A1 | 4/2007 | Kraus et al. | |
| 2008/0245758 A1 | 10/2008 | Geser et al. | |
| 2008/0287914 A1 | 11/2008 | Wyatt et al. | |
| 2010/0179506 A1 | 7/2010 | Shemesh et al. | |
| 2010/0217226 A1 | 8/2010 | Shemesh | |
| 2011/0062703 A1 | 3/2011 | Lopez et al. | |
| 2011/0074148 A1 | 3/2011 | Imai | |
| 2011/0106046 A1 | 5/2011 | Hiranuma et al. | |
| 2011/0257621 A1 | 10/2011 | Fangrow | |
| 2011/0291406 A1 | 12/2011 | Kraft et al. | |
| 2012/0035580 A1 | 2/2012 | Fangrow | |
| 2012/0046636 A1 | 2/2012 | Kriheli | |
| 2012/0123381 A1 | 5/2012 | Kraus et al. | |
| 2012/0192968 A1 | 8/2012 | Bonnal et al. | |
| 2012/0203193 A1 | 8/2012 | Rogers | |
| 2012/0265163 A1 | 10/2012 | Cheng et al. | |
| 2012/0279884 A1 | 11/2012 | Tennican et al. | |
| 2012/0316536 A1 | 12/2012 | Carrez et al. | |
| 2013/0006211 A1 | 1/2013 | Takemoto | |
| 2013/0012908 A1 | 1/2013 | Yeung | |
| 2013/0066293 A1 | 3/2013 | Garfield et al. | |
| 2013/0072893 A1 | 3/2013 | Takemoto | |
| 2013/0076019 A1 | 3/2013 | Takemoto | |
| 2013/0079744 A1 | 3/2013 | Okiyama et al. | |
| 2014/0261861 A1 * | 9/2014 | Ivosevic | A61J 1/2096 141/2 |

(56) References Cited

U.S. PATENT DOCUMENTS

| | | |
|---|---|---|
| 2014/0261877 A1 | 9/2014 | Ivosevic et al. |
| 2014/0352845 A1 | 12/2014 | Lev et al. |
| 2017/0143587 A1* | 5/2017 | Ivosevic ............... A61J 1/2096 |

FOREIGN PATENT DOCUMENTS

| | | |
|---|---|---|
| WO | 8404673 A1 | 12/1984 |
| WO | 2006103074 A1 | 10/2006 |
| WO | 2009024807 A1 | 2/2009 |
| WO | 2009090627 A1 | 7/2009 |
| WO | 2009133755 A1 | 11/2009 |
| WO | 2011050333 A1 | 4/2011 |
| WO | 2012069401 A1 | 5/2012 |
| WO | 2012119225 A1 | 9/2012 |
| WO | 2013115730 A1 | 8/2013 |
| WO | 2013179596 A1 | 12/2013 |

* cited by examiner

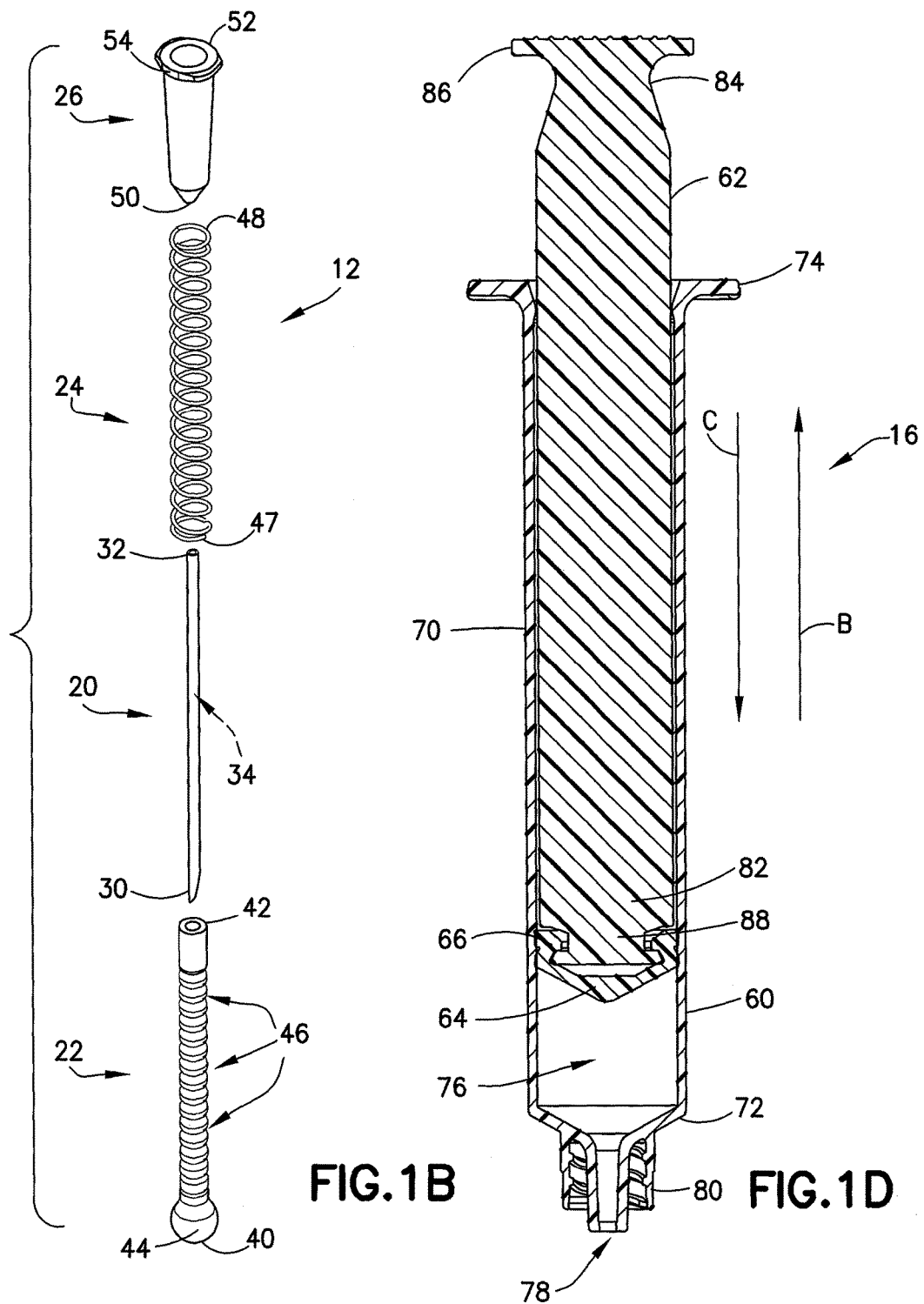

SEAL SYSTEM FOR CANNULA

CROSS-REFERENCE TO RELATED APPLICATION

This application is a continuation application of U.S. patent application Ser. No. 14/204,383, filed Mar. 11, 2014, which claims priority to U.S. Provisional Application Ser. No. 61/787,674, filed Mar. 15, 2013, each of which are hereby incorporated by reference in their entirety.

BACKGROUND OF THE INVENTION

1. Field of the Disclosure

The present disclosure relates generally to a seal system for a cannula. More particularly, the present disclosure relates to a cannula seal that prevents exposure of a liquid residue on the cannula tip during use.

2. Description of the Related Art

Health care providers reconstituting, transporting, and administering hazardous drugs, such as cancer treatments, can put health care providers at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. These exposures can be as dangerous to a nurse's health as being accidently stuck with a needle. In order to reduce the risk of health care providers being exposed to toxic drugs, protection and sealing of cannulas becomes important.

SUMMARY OF THE INVENTION

In one embodiment, a system includes a needle hub having a proximal end and a distal end with the proximal end of the needle hub having a connection portion configured to receive a first container. A cannula is received by the needle hub with the cannula having a proximal end and a distal end. The system also includes a cannula seal having a resilient sleeve enclosing at least a portion of the cannula and a vial adapter configured to be attached to a second container with the vial adapter having a vial seal that is configured to engage the cannula seal. The cannula seal has a first position where the cannula seal encloses the distal end of the cannula and a second position where the cannula seal is retracted to expose the distal end of the cannula.

The system may further include a vial defining a vial chamber with a first substance contained within the vial chamber. The vial includes a vial septum engaged with the vial to seal the first substance within the vial chamber. The vial adapter is configured to be attached to the vial. The vial adapter may be attached to the vial such that the vial seal is aligned with the vial septum. The cannula seal may be in communication with the vial seal with the cannula configured to pierce the cannula seal, the vial seal, and the vial septum to place the vial chamber in fluid communication with the barrel chamber via the cannula, and when the cannula is removed from the vial, as the cannula is withdrawn from the vial seal, the cannula seal elastically encloses the cannula simultaneously with the cannula exiting the vial seal. The system may include a syringe barrel defining a barrel chamber with the connection portion of the needle hub configured to receive the syringe barrel. The vial chamber may be in fluid communication with the barrel chamber with the first substance capable of being transferred from the vial chamber to the barrel chamber via the cannula.

The system may include a spring disposed over the cannula seal such that the cannula seal is positioned between the cannula and the spring with the spring biasing the cannula seal to the first position. Alternatively, a spring may be disposed over the cannula such that the spring is positioned between the cannula and the cannula seal with the spring biasing the cannula seal to the first position. A cannula stabilizing member may be disposed over a portion of the cannula with the cannula stabilizing member enclosed within the cannula seal. When the cannula seal is in the first position, the cannula seal may extend from the needle hub to a position beyond the distal end of the cannula. The vial seal may be a resilient seal. The system may further include an aspiration arrangement configured to allow air to be aspirated into a syringe barrel when a syringe barrel is connected to the connection portion of the needle hub. The aspiration arrangement may include a one-way valve and a filter. The needle hub may include an inner wall and an outer wall that define an annular recess with the needle hub defining a passageway extending through the outer wall and the inner wall. The filter may be positioned within the annular recess. The one-way valve may be formed by an extension of the cannula seal that extends into the needle hub. The cannula seal may include an open proximal end and a distal end with the distal end of the cannula seal including a rounded head portion. The cannula seal may include a plurality of annular rib members. The vial adapter may include a body having an adhesive configured to secure the vial adapter to the second container. The vial seal of the vial adapter may define a concave recess that is configured to a corresponding portion of the cannula seal. The vial seal of the vial adapter may define a concave recess that is configured to receive the rounded head portion of the distal end of the cannula seal.

In a further embodiment, a method of transferring fluids between first and second containers includes providing a needle hub, a cannula received by the needle hub, and a cannula seal enclosing at least a portion of the cannula with the cannula seal having a first position where the cannula seal encloses a distal end of the cannula and a second position where the distal end of the cannula is positioned outside of the cannula seal. The method includes securing the needle hub to the first container and attaching a vial adapter to the second container with the vial adapter having a vial seal. The method also includes engaging the vial seal of the vial adapter with the cannula seal and piercing the cannula seal and the vial seal with the cannula such that the cannula is in fluid communication with the second container, with the cannula seal moving from the first position to the second position, and transferring fluid from the second container to the first container. The method further includes withdrawing the cannula from the second container and disengaging the cannula seal from the vial seal of the vial adapter with the cannula seal returning to the first position.

The method may further include aspirating air into the first container after securing the needle hub to the first container.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1B is an exploded perspective view of a cannula seal assembly in accordance with an embodiment of the present invention.

FIG. 1D is a cross-sectional view of a barrel assembly of FIG. 1A with a stopper slidably disposed within a barrel and a plunger rod engaged with a portion of the stopper in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1A:
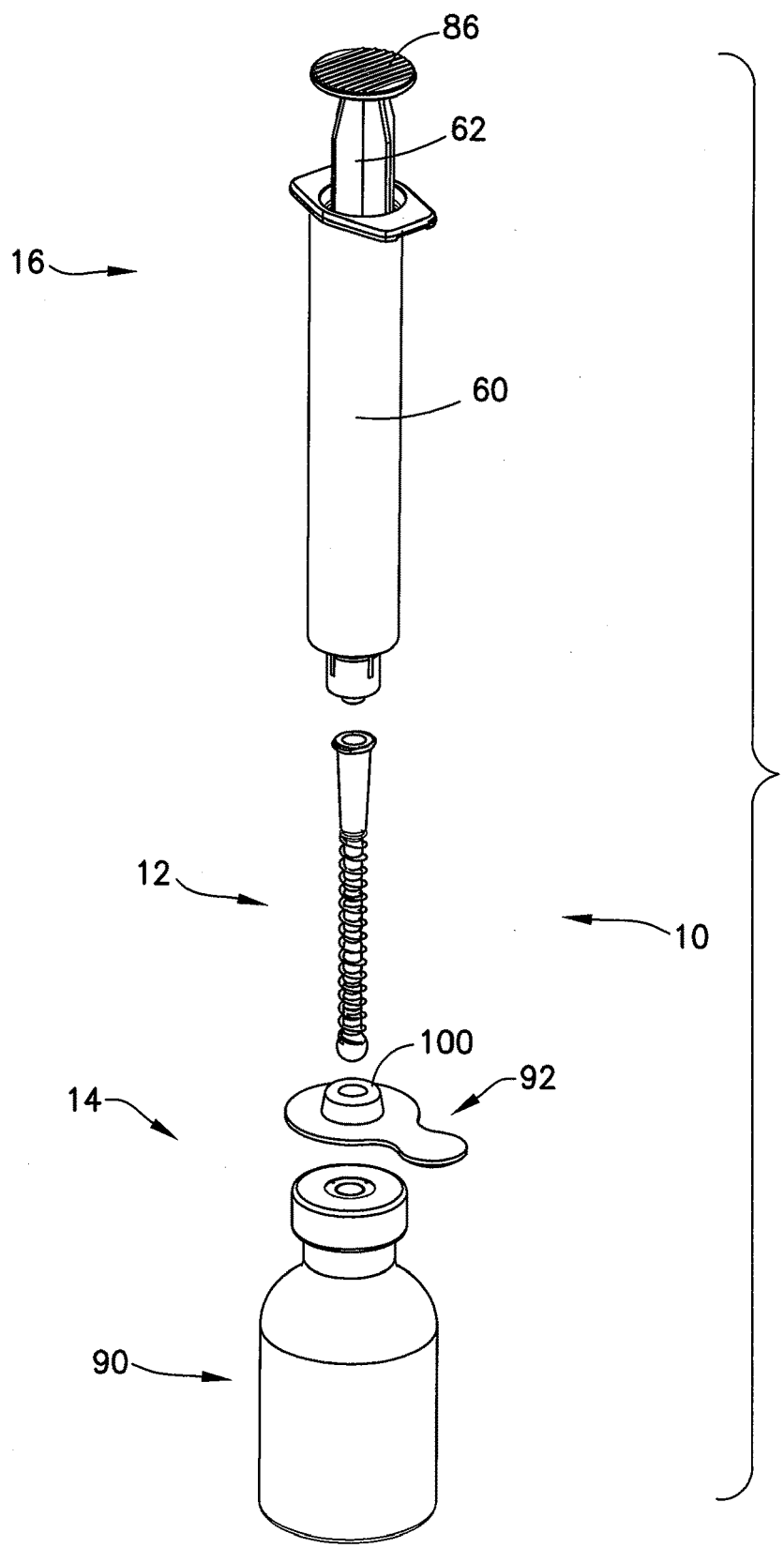
FIG. 1A is an exploded perspective view of a seal system in accordance with an embodiment of the present invention.
Figure 1C:
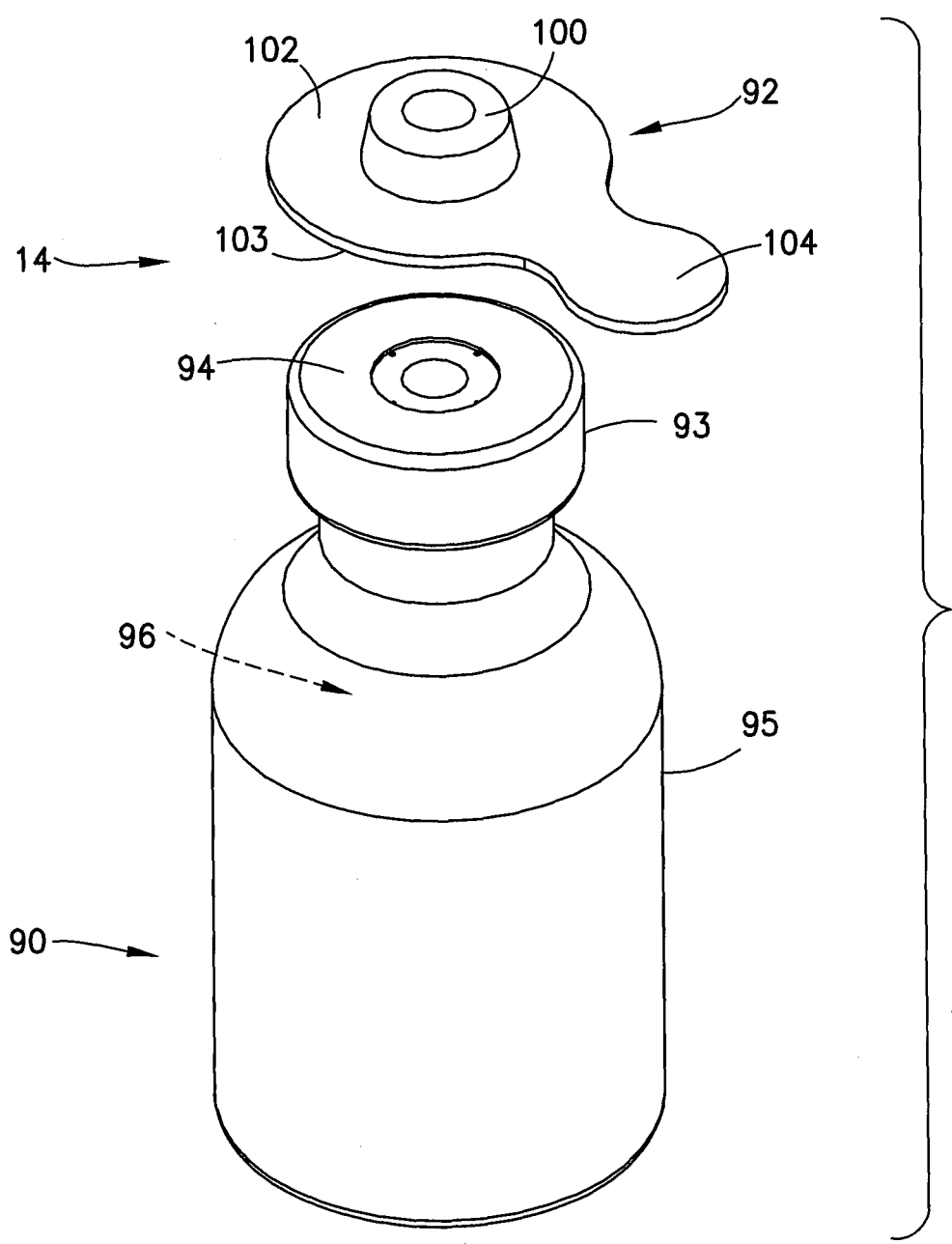
FIG. 1C is an exploded perspective view of a vial seal assembly in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a barrel adapted for contact with a patient and/or engagement with a separate device such as a needle assembly or IV connection assembly, and "proximal" refers to the opposite direction of distal, i.e., away from the end of a barrel adapted for engagement with the separate device. For purposes of this disclosure, the above-mentioned references are used in the description of the components of a barrel in accordance with the present disclosure.

FIGS. 1A-8 illustrate an exemplary embodiment of the present disclosure. Referring to FIGS. 1A-8, seal system 10 includes a cannula seal assembly 12, a vial seal assembly 14, and a barrel assembly 16 as will be described in more detail below. Seal system 10 provides leak-proof sealing during engagement of a cannula with a vial, during transfer of a substance from a vial chamber to a barrel chamber via the cannula, and during disengagement of the cannula from the vial. The leak-proof sealing of the system 10 substantially prevents leakage of both air and liquid during use of the system 10. Seal system 10 is compatible with a needle and syringe assembly for accessing a medication contained within a vial for administering the medication to a patient. Seal system 10 is also compatible to be used with a drug reconstitution system as will be described in more detail below.

Referring to FIGS. 1B and 4-8, cannula seal assembly 12 includes a cannula 20, a cannula seal 22, a spring 24, and a needle hub 26. Referring to FIG. 1B, cannula 20 includes a distal end 30, a proximal end 32, and a lumen 34 extending therebetween. Distal end 30 is in fluid communication with proximal end 32 via lumen 34 of cannula 20. Distal end 30 of cannula 20 is capable of piercing cannula seal 22, a vial seal 100, and a vial septum 94 to place a vial chamber 96 in fluid communication with a barrel chamber 76 via cannula 20 as will be described in more detail below. In one embodiment, distal end 30 of cannula 20 defines a sharp point.

Figure 4:
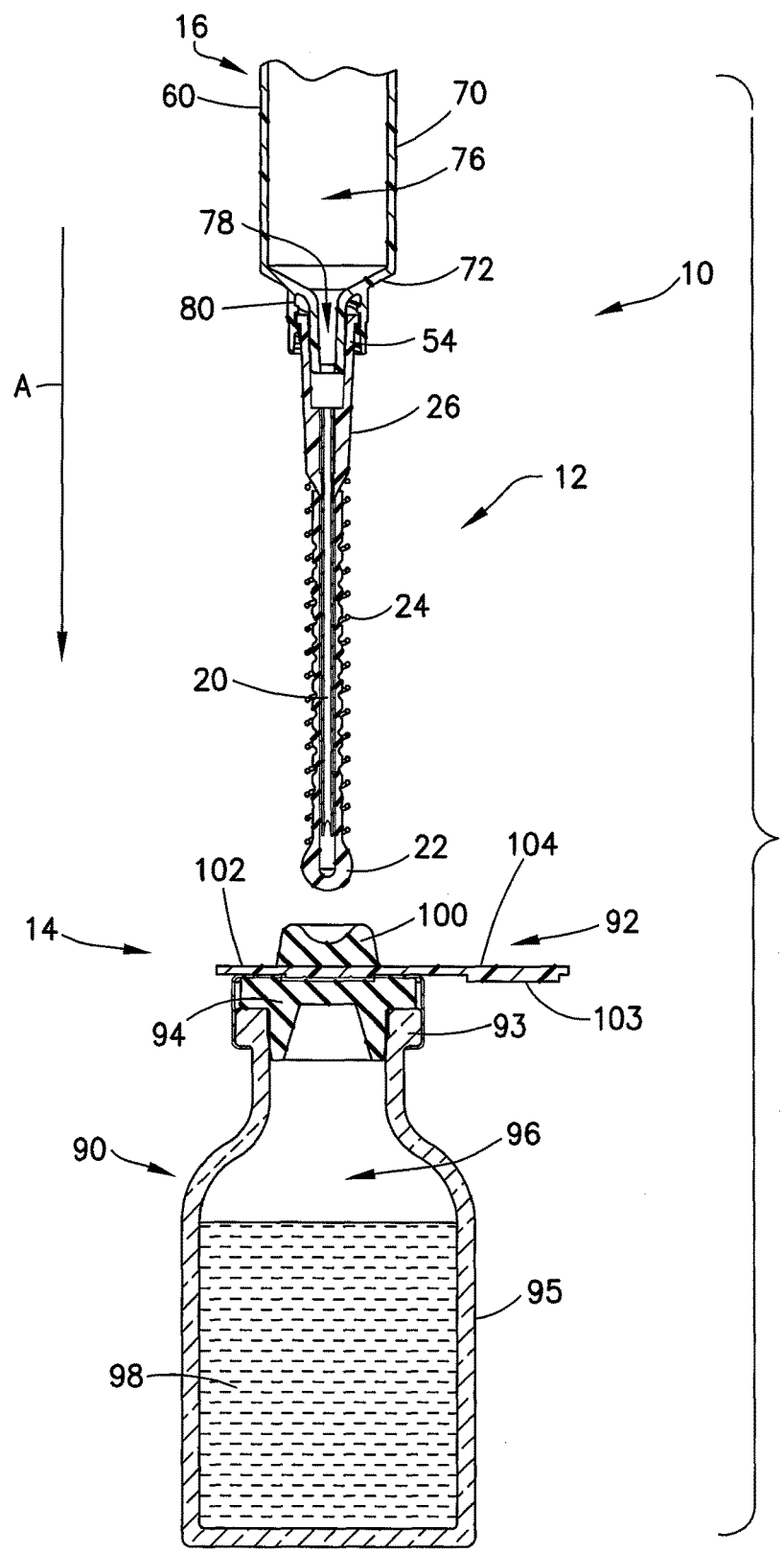
FIG. 4 is a cross-sectional view of the seal system of FIG. 3 with the cannula seal not in communication with the vial seal in accordance with an embodiment of the present invention.
Figure 6:
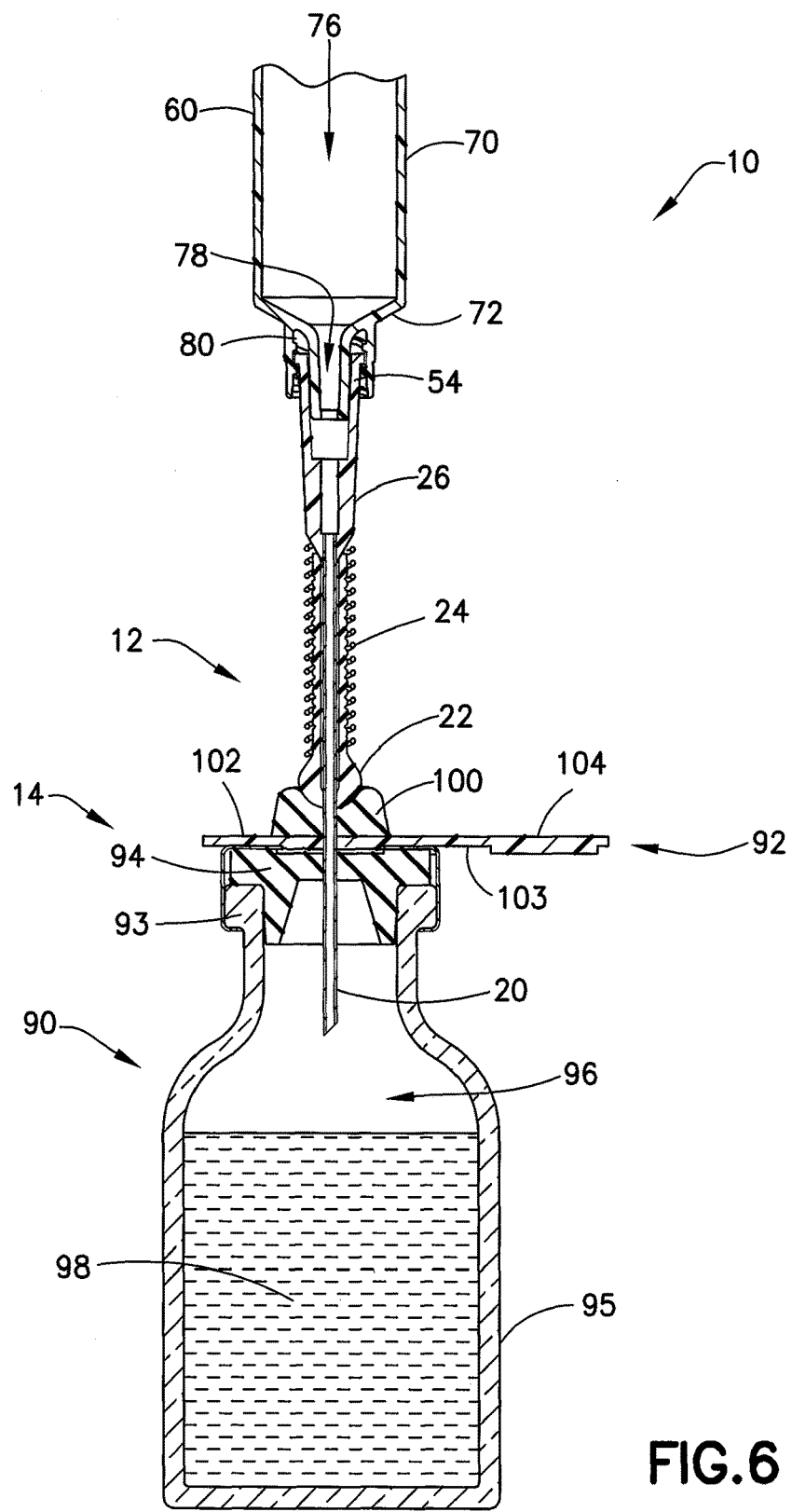
FIG. 6 is a cross-sectional view of the seal system of FIG. 3 with the cannula seal in communication with the vial seal and a cannula piercing the cannula seal, the vial seal, and a vial septum to place a vial chamber in fluid communication with a barrel chamber via the cannula in accordance with an embodiment of the present invention.
Figure 7:
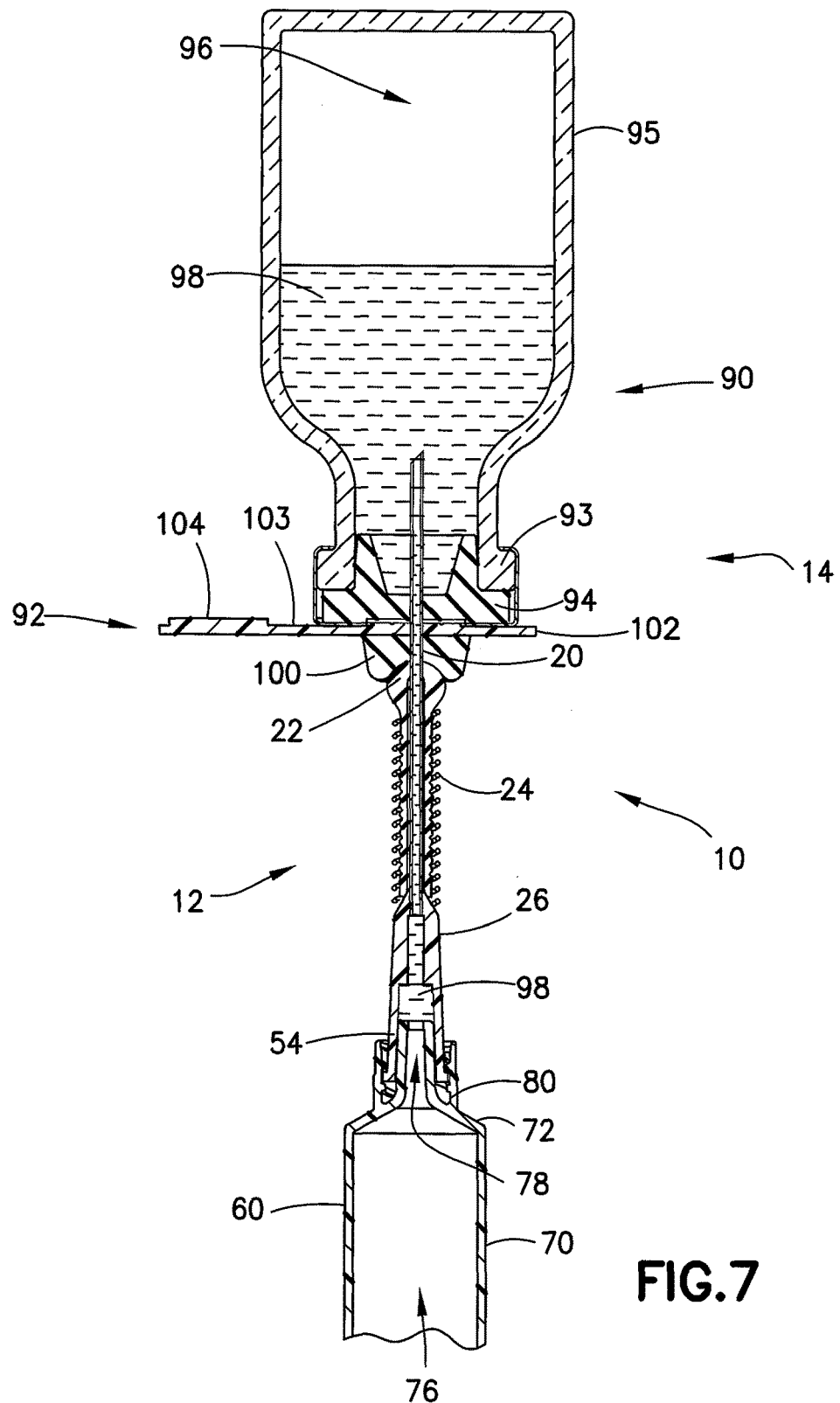
FIG. 7 is a cross-sectional view of the seal system of FIG. 3 with the seal system inverted and the cannula seal in communication with the vial seal and a cannula in fluid communication with a substance contained within a vial chamber in accordance with an embodiment of the present invention.
Figure 8:
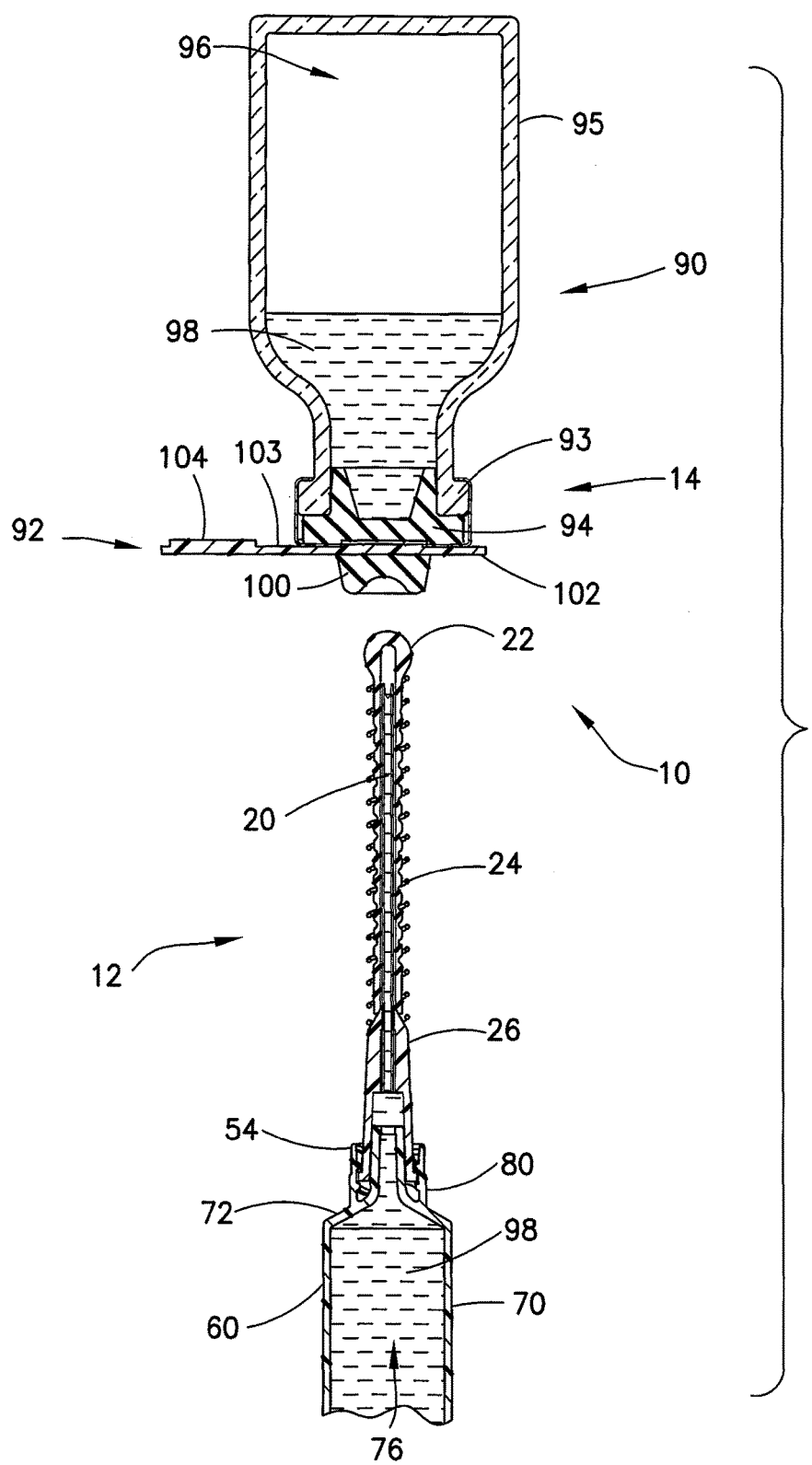
FIG. 8 is a cross-sectional view of the seal system of FIG. 3 with the seal system inverted and the cannula seal not in communication with the vial seal and a portion of a substance contained within a vial chamber transferred to a barrel chamber via a cannula in accordance with an embodiment of the present invention.

Referring to FIGS. 1B and 4-8, cannula seal 22 generally includes a self-sealing seal secured over cannula 20 so that cannula seal 22 encloses cannula 20 in a sealed position (FIGS. 4 and 8) to provide a leak-proof seal preventing any liquid, air, or medication residue from being exposed to a health care provider reconstituting, transporting, or administering a drug using cannula seal assembly 12. Referring to FIGS. 4 and 8, with cannula seal 22 in the sealed position, cannula seal 22 encloses cannula 20 to also prevent accidental needle stick injuries to a user of cannula seal assembly 12. Referring to FIG. 1B, cannula seal 22 includes a distal end 40, a proximal end 42, and annular ribbed members 46. In one embodiment, distal end 40 of cannula seal 22 includes a head portion 44. Although FIG. 1B illustrates head portion 44 of cannula seal 22 as a rounded portion, it is contemplated that other shapes and sizes of head portion 44 may be used. For example, head portion 44 can have other multi-sided polygon cross-sectional shapes, such as square or rectangular cross-sectional shapes.

In one embodiment, cannula seal 22 comprises a resilient material. For example, cannula seal 22 is preferably a unitary device molded of any flexible, elastomeric material conventionally used for fabricating gas-proof closures. In particular, cannula seal 22 may be formed of an elastomeric material including rubber, silicone based elastomer, and thermoplastic elastomer, or similar materials. It is contemplated that cannula seal 22 is formed of a material having a Shore A hardness of approximately 10 to 50. It is also envisioned that cannula seal 22 can have other material hardness values that would provide an appropriate self-sealing material to provide a leak-proof seal with cannula seal 22 in the sealed position, thereby preventing any liquid or medication residue from being exposed to a health care provider reconstituting, transporting, or administering a drug using cannula seal assembly 12. In one embodiment, cannula seal 22 comprises a resilient sleeve.

Figure 2:
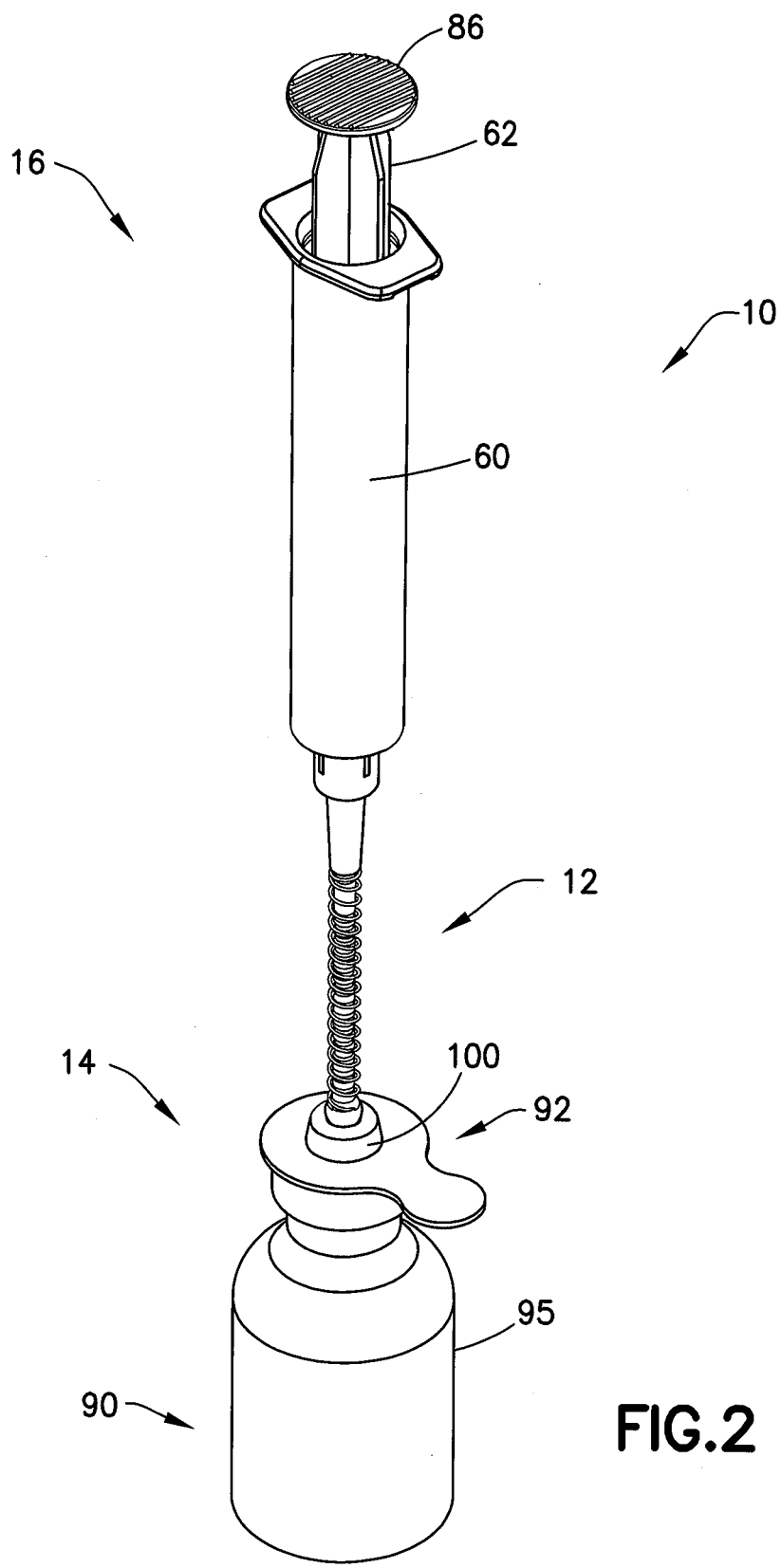
FIG. 2 is an assembled perspective view of the seal system of FIG. 1A in accordance with an embodiment of the present invention.
Figure 3:
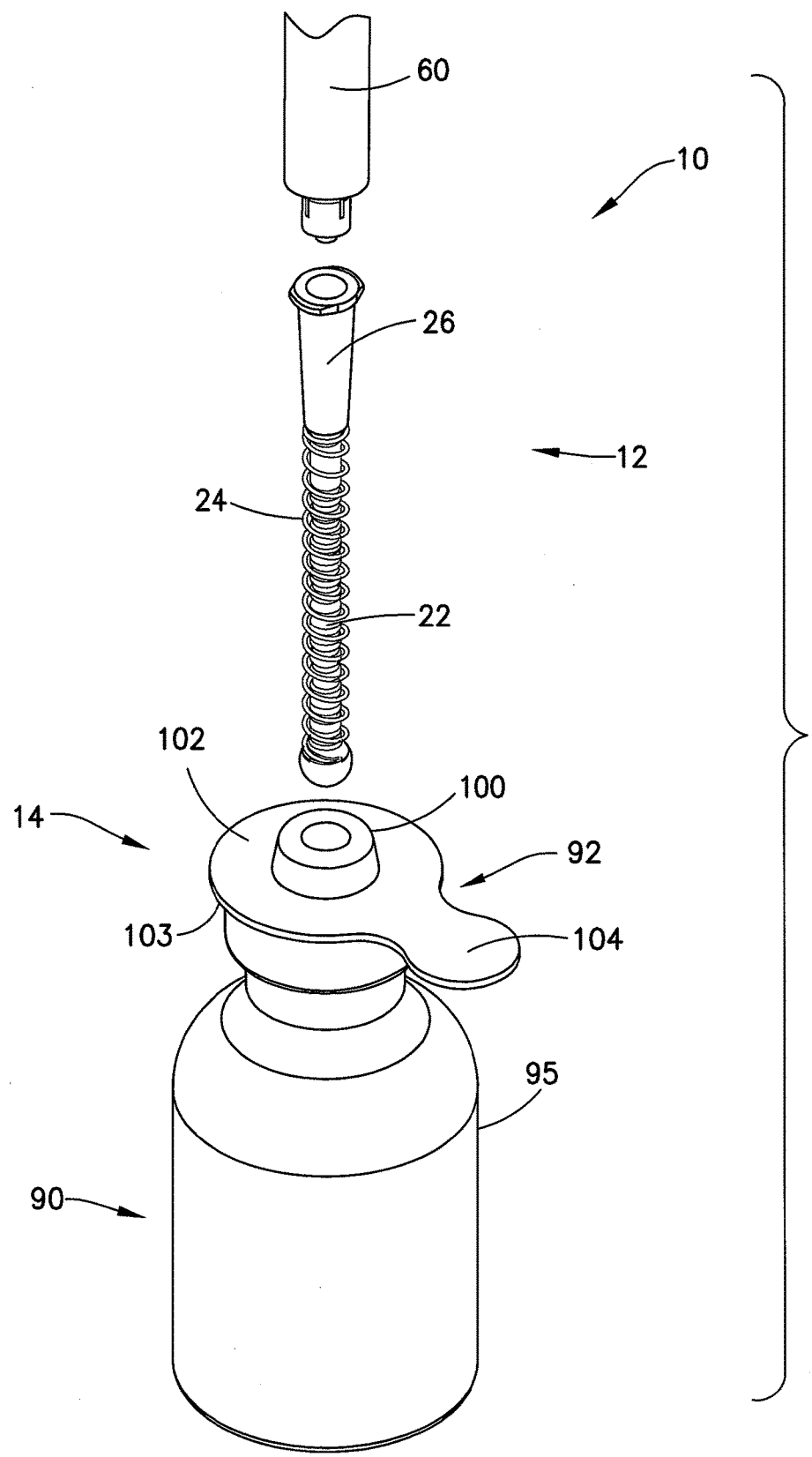
FIG. 3 is a fragmentary, perspective view of the seal system of FIG. 2 with a cannula seal not in communication with a vial seal in accordance with an embodiment of the present invention.

Referring to FIGS. 1B and 2-8, spring 24 includes a distal end 47 and proximal end 48. Spring 24 provides a biasing force that promotes cannula seal 22 to enclose cannula 20 in the sealed position as will be described in more detail below. Referring to FIGS. 2-8, spring 24 is disposed over cannula seal 22 such that cannula seal 22 is between cannula 20 and spring 24. Referring to FIGS. 2-4, spring 24 is disposed over cannula seal 22 such that distal end 47 of spring 24 engages head portion 44 of cannula seal 22. In one embodiment, head portion 44 of cannula seal 22 has a larger diameter than spring 24 so that spring 24 exerts the biasing force on head portion 44 of cannula seal 22. The spring 24 may be biased or compressed slightly upon assembly of the cannula seal assembly 12. Head portion 44 of cannula seal 22 also ensures that spring 24 is secured between head portion 44 and needle hub 26.

Referring to FIGS. 1B and 4-8, needle hub 26 generally includes a distal end 50 and a proximal end 52. Proximal end 52 of needle hub 26 includes a barrel connection portion 54. In one embodiment, barrel connection portion 54 is a threaded portion. Referring to FIGS. 4-8, needle hub 26 supports a portion of cannula 20. Distal end 50 of needle hub 26 also provides a connection with proximal end 48 of spring 24 so that distal end 47 of spring 24 may be compressed relative to proximal end 48 of spring 24 when cannula 20 pierces cannula seal 22 as will be described in more detail below. With spring 24 compressed, spring 24 exerts a biasing force that promotes cannula seal 22 to elastically enclose cannula 20. Referring to FIGS. 4 and 8, in one embodiment, with cannula seal 22 in the sealed position, spring 24 is loaded between head portion 44 of cannula seal 22 and needle hub 26 in a slightly compressed position so that spring 24 exerts a biasing force that retains cannula seal 22 in the sealed position.

Figure 5:
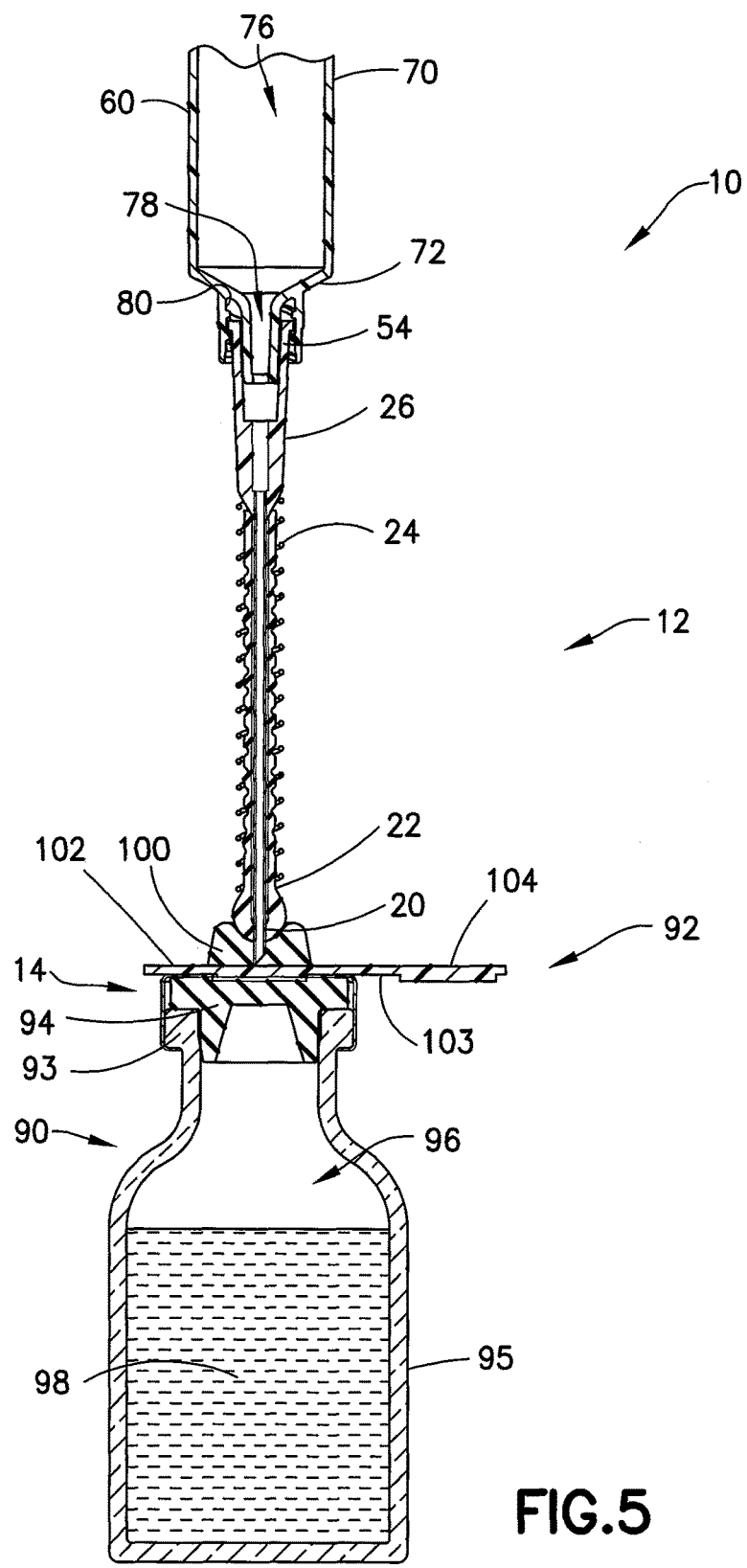
FIG. 5 is a cross-sectional view of the seal system of FIG. 3 with the cannula seal in communication with the vial seal in accordance with an embodiment of the present invention.

In one embodiment, referring to FIGS. 2-8, annular ribbed members 46 of cannula seal 22 provide an additional biasing force that retains cannula seal 22 in the sealed position. Referring to FIGS. 4-6, as cannula 20 is brought into contact with vial seal assembly 14, annular ribbed members 46 of cannula seal 22 and spring 24 are compressed as cannula 20 pierces cannula seal 22 and vial seal assembly 14. With annular ribbed members 46 of cannula seal 22 compressed, annular ribbed members 46 exert an additional biasing force that promotes cannula seal 22 to elastically enclose cannula 20.

Referring to FIGS. 1B and 4-8, proximal end 52 of needle hub 26 is attached to a barrel 60 of barrel assembly 16. With needle hub 26 supporting a portion of cannula 20 and with proximal end 52 of needle hub 26 attached to barrel 60 of barrel assembly 16, needle hub 26 attaches cannula 20 to barrel assembly 16 such that cannula 20 is in fluid communication with barrel chamber 76 of barrel 60 as will be described in more detail below.

Referring to FIG. 1D, barrel assembly 16 includes barrel 60, a plunger rod 62, and a stopper 64. Barrel assembly 16 may be adapted for the dispensing and delivery of a fluid and/or collection of a fluid. For example, barrel assembly 16 may be used for injection or infusion of fluid such as a medication into a patient. Barrel assembly 16 is contemplated for use in connection with a needle, such as by connecting barrel assembly 16 to cannula 20 as described, connecting barrel assembly 16 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container or vial, and the like.

Referring to FIG. 1D, barrel 60 generally includes a barrel body or sidewall 70 extending between a first or distal end 72 and a second or proximal end 74. Sidewall 70 defines an elongate aperture or barrel chamber 76 of barrel 60. In one embodiment, barrel chamber 76 may span the extent of barrel 60 so that barrel 60 is cannulated along its entire length. In one embodiment, barrel 60 may be in the general form of an elongated cylindrical barrel as is known in the art in the general shape of a hypodermic syringe. In alternative embodiments, barrel 60 may be in other forms for containing a fluid for delivery, such as in the general form of an elongated rectangular barrel, for example. Barrel 60 may be formed of glass, or may be injection molded from thermoplastic material such as polypropylene and polyethylene according to techniques known to those of ordinary skill in the art, though it is to be appreciated that barrel 60 may be made from other suitable materials and according to other applicable techniques.

Referring to FIG. 1D, distal end 72 of barrel 60 includes an outlet opening 78 which is in fluid communication with barrel chamber 76. Outlet opening 78 may be sized and adapted for engagement with a separate device, such as cannula 20, a needle assembly, or IV connection assembly and, therefore, may include a mechanism for such engagement as is conventionally known. For example, distal end 72 may include a generally-tapered luer tip for engagement with an optional separate tapered luer mating surface of such a separate device for attachment therewith (not shown). Distal end 72 of barrel 60 also includes a mechanism for locking engagement with needle hub 26, such as a needle hub connection portion 80. In one embodiment, needle hub connection portion 80 is a threaded portion. Referring to FIGS. 4-8, needle hub 26 is attached to barrel 60 by securing barrel connection portion 54 of needle hub 26 to needle hub connection portion 80 of barrel 60.

Proximal end 74 of barrel 60 is generally open-ended, but is intended to be closed off to the external environment as will be discussed herein. Barrel 60 may also include fill lines, such as graduations located on sidewall 70, for providing an indication as to the level or amount of fluid contained within barrel chamber 76 of barrel 60. Such markings may be provided on an external surface of sidewall 70, an internal surface of sidewall 70, or integrally formed or otherwise within sidewall 70 of barrel 60. In other embodiments, alternatively, or in addition thereto, the markings may also provide a description of the contents of the syringe or other identifying information such as maximum and/or minimum fill lines.

Referring to FIG. 1D, barrel assembly 16 includes stopper 64 which is movably or slidably disposed within barrel chamber 76, and in sealing contact with the internal surface of sidewall 70 of barrel 60. Stopper 64 is sized relative to barrel 60 to provide sealing engagement with the interior surface of sidewall 70 of barrel 60. Additionally, stopper 64 may include one or more annular ribs extending around the periphery of stopper 64 to increase the sealing engagement between stopper 64 and the interior surface of sidewall 70 of barrel 60.

Referring to FIG. 1D, in one embodiment, stopper 16 also includes an engagement portion 66 for securing plunger rod 62 to stopper 64. In one embodiment, engagement portion 66 of stopper 64 may include a threaded portion for engagement with a threaded portion of plunger rod 62. In other embodiments, engagement portion 66 of stopper 64 may include a snap fit mechanism, a ball detent, locking tabs, spring loaded locking mechanism, latch, adhesive, or other similar mechanism. In another embodiment, plunger rod 62 and stopper 64 may be co-formed such as by co-extrusion.

Referring to FIG. 1D, barrel assembly 16 includes plunger rod 62 which provides a mechanism for dispensing fluid contained within barrel chamber 76 of barrel 60 through outlet opening 78 to cannula 20 upon connection of plunger rod 62 to barrel 60 via stopper 64. Plunger rod 62 is adapted for advancing stopper 64. In one embodiment, plunger rod 62 is sized for movement within barrel chamber 76 of barrel 60 to actuate stopper 64 between a first position adjacent distal end 72 of barrel 60 and a second position adjacent proximal end 74 of barrel 60. Referring to FIG. 1D, plunger rod 62 includes a distal end 82, a proximal end 84, a flange portion 86 disposed at proximal end 84, and a securement feature or engagement portion 88 for securing plunger rod 62 to stopper 64 as described above.

Referring to FIGS. 1C and 4-8, vial seal assembly 14 includes a vial 90 and a vial adapter 92. Referring to FIGS. 1C and 4-8, vial 90 may be a standard drug vial of any type having an open head portion 93 covered by a pierceable septum 94 of an elastomeric material. Walls 95 of vial 90 define vial chamber 96 for containing a substance 98. Vial septum 94 is engaged with head portion 93 of vial 90 to seal the substance 98 within vial chamber 96.

Referring to FIGS. 1C and 4-8, vial adapter 92 includes vial seal 100, a body portion 102 having an interior surface 103, and a handle portion 104. Interior surface 103 of body portion 102 of vial adapter 92 is attachable to vial 90. In one embodiment, interior surface 103 is coated with an adhesive for attaching vial adapter 92 to vial 90. In one embodiment, referring to FIGS. 4-8, with vial seal 100 of vial adapter 92 aligned with vial septum 94 of vial 90, interior surface 103 can be pressed onto head portion 93 of vial 90 and the adhesive attaches vial adapter 92 to vial 90. In other embodiments, the interior surface 103 may include other connection mechanisms for securing vial adapter 92 to vial 90 such as a threaded portion, a snap fit mechanism, locking tabs, or other similar mechanism.

Referring to FIGS. 1C and 4-8, vial seal 100 generally includes a self-sealing seal that, with vial adapter 92 attached to vial 90 such that vial seal 100 is aligned with vial septum 94, provides a leak-proof seal preventing any substance contained within vial chamber 96 from being exposed to a health care provider reconstituting, transporting, or administering a drug using vial seal assembly 14. Referring to FIGS. 5-7, with vial seal 100 in communication with cannula seal 22, vial seal 100 and cannula seal 22 provide a leak-proof seal that is liquid tight and airtight preventing any substance residue from being exposed to a health care provider while reconstituting or withdrawing substance 98 from vial 90 to barrel 60 via cannula 20 as will be described in more detail below.

In one embodiment, vial seal 100 comprises a resilient material. For example, vial seal 100 is preferably a unitary device molded of any flexible, elastomeric material conventionally used for fabricating gas-proof closures. Vial seal 100 may be formed of a natural rubber material, polyurethane elastomers, butyl rubbers, or similar materials. It is contemplated that vial seal 100 is formed of a material having a Shore A hardness of approximately 10 to 50. It is also envisioned that vial seal 100 can have other material hardness values that would provide an appropriate self-sealing material to provide a leak-proof seal with vial septum 94 of vial 90 and cannula seal 22, thereby preventing any liquid or medication residue from being exposed to a health care provider reconstituting, transporting, or administering a drug using seal system 10.

FIGS. 9-18 illustrate another exemplary embodiment of the present disclosure. The embodiment illustrated in FIGS. 9-18 includes similar components to the embodiment illustrated in FIGS. 1A-8, and the similar components are denoted by a reference number followed by the letter A. For the sake of brevity, these similar components and the similar steps of using seal system 10A (FIGS. 9-18) will not all be discussed in conjunction with the embodiment illustrated in FIGS. 9-18.

Referring to FIGS. 9-18, seal system 10A includes a cannula seal assembly 110, vial seal assembly 14A, and barrel assembly 16A as will be described in more detail below. Seal system 10A provides leak-proof sealing during engagement of a cannula with a vial, during transfer of a substance from the vial chamber to the barrel chamber via the cannula, and during disengagement of the cannula from the vial. Seal system 10A is compatible with a needle and syringe assembly for accessing a medication contained within a vial for administering the medication to a patient. Seal system 10A is also compatible to be used with a drug reconstitution system as will be described in more detail below.

Figure 14:
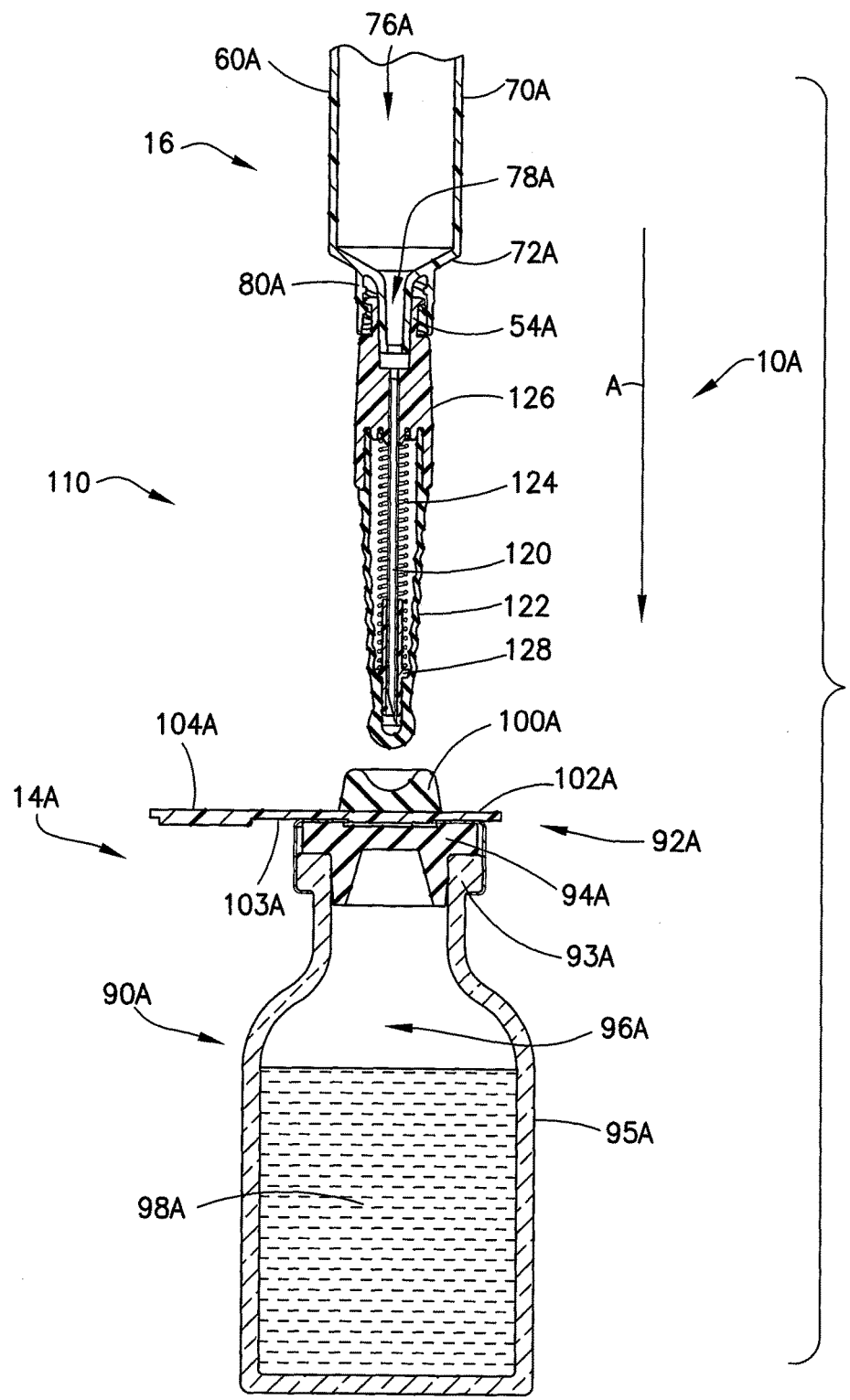
FIG. 14 is a cross-sectional view of the seal system of FIG. 13 with the cannula seal not in communication with the vial seal in accordance with an embodiment of the present invention.

Referring to FIGS. 9-18, cannula seal assembly 110 includes a cannula 120, a cannula seal 122, a spring 124, a needle hub 126, and cannula stabilizing member 128. Referring to FIG. 11B, cannula 120 includes a distal end 130, a proximal end 132, and a lumen 134 extending therebetween. Distal end 130 is in fluid communication with proximal end 132 via lumen 134 of cannula 120. As seen in FIG. 14, distal end 130 of cannula 120 is capable of piercing cannula seal 122, a vial seal 100A, and a vial septum 94A to place a vial chamber 96A in fluid communication with a barrel chamber 76A via cannula 120 as will be described in more detail below. In one embodiment, distal end 130 of cannula 120 defines a sharp point.

Figure 18:
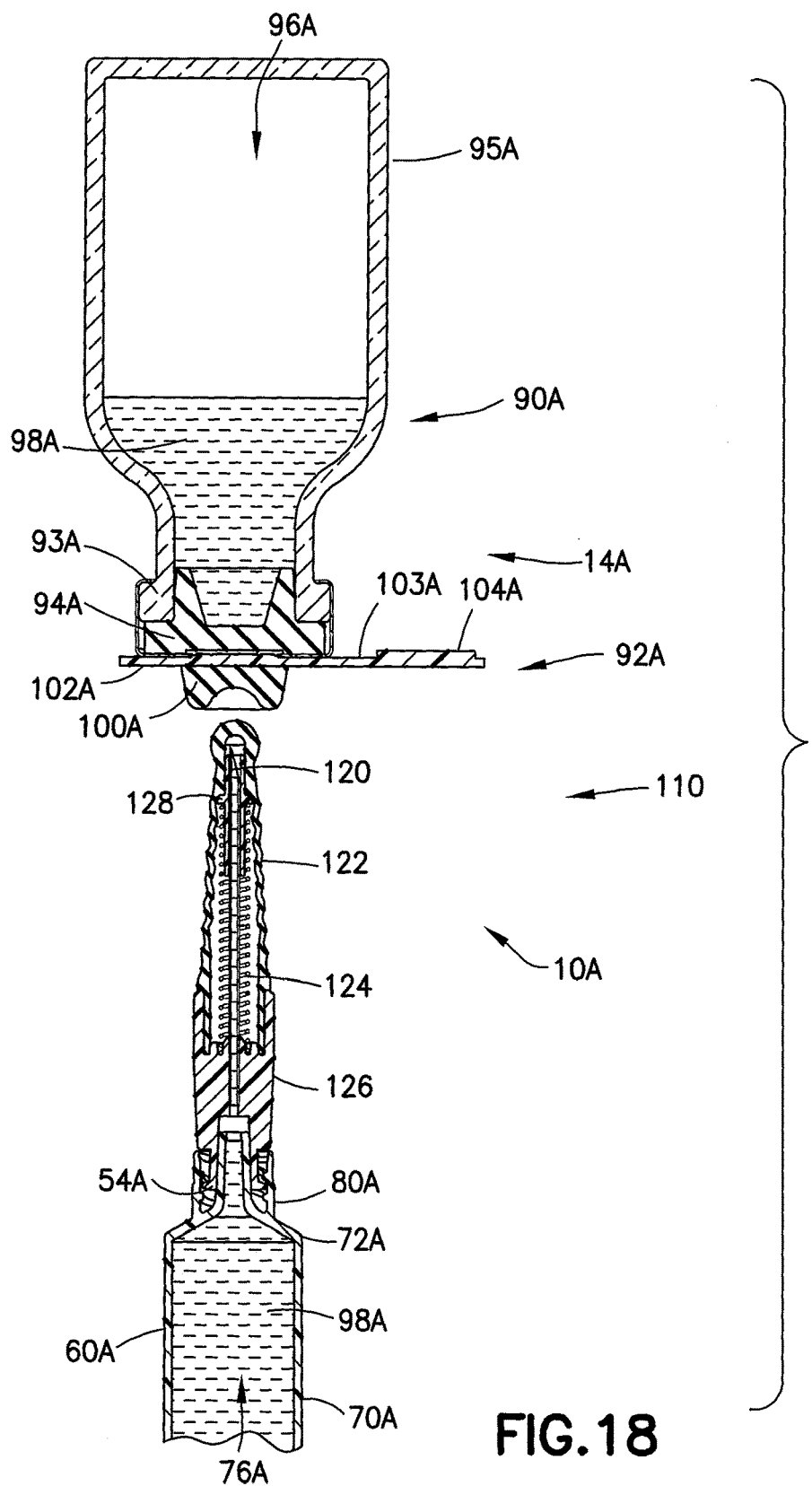
FIG. 18 is a cross-sectional view of the seal system of FIG. 13 with the seal system inverted and the cannula seal not in communication with the vial seal and a portion of a substance contained within a vial chamber transferred to a barrel chamber via a cannula in accordance with an embodiment of the present invention.

Referring to FIGS. 9-18, cannula seal 122 generally includes a self-sealing seal secured over cannula 120 so that cannula seal 122 encloses cannula 120 in a sealed position (FIGS. 14 and 18) to provide a leak-proof seal preventing any liquid, air, or medication residue from being exposed to a health care provider reconstituting, transporting, or administering a drug using cannula seal assembly 110. Referring to FIGS. 14 and 18, with cannula seal 122 in the sealed position, cannula seal 122 encloses cannula 120 to also prevent accidental needle stick injuries to a user of cannula seal assembly 110. Cannula seal 122 includes a distal end 140, a proximal end 142, annular ribbed members 146 extending therebetween, and a shoulder portion 144 (FIGS. 9 and 10) located on an interior wall 148 near distal end 140 of cannula seal 122.

In one embodiment, cannula seal 122 comprises a resilient material. For example, cannula seal 122 is preferably a unitary device molded of any flexible, elastomeric material conventionally used for fabricating gas-proof closures. Cannula seal 122 may be formed of a natural rubber material, polyurethane elastomers, butyl rubbers, or similar materials. It is contemplated that cannula seal 122 is formed of a material having a Shore A hardness of approximately 10 to 50. It is also envisioned that cannula seal 122 can have other material hardness values that would provide an appropriate self-sealing material to provide a leak-proof seal with cannula seal 122 in the sealed position, thereby preventing any liquid or medication residue from being exposed to a health care provider reconstituting, transporting, or administering a drug using cannula seal assembly 110. In one embodiment, cannula seal 122 comprises a resilient sleeve.

Referring to FIGS. 9, 10, and 14-18, spring 124 includes a distal end 160 and a proximal end 162. Spring 124 provides a biasing force that promotes cannula seal 122 to enclose cannula 120 in the sealed position as will be described in more detail below. Referring to FIGS. 9, 10, and 14-18, spring 124 is disposed over cannula 120 such that spring 124 is between cannula 120 and cannula seal 122, i.e., cannula seal 122 encloses spring 124 and cannula 120.

Figure 10:
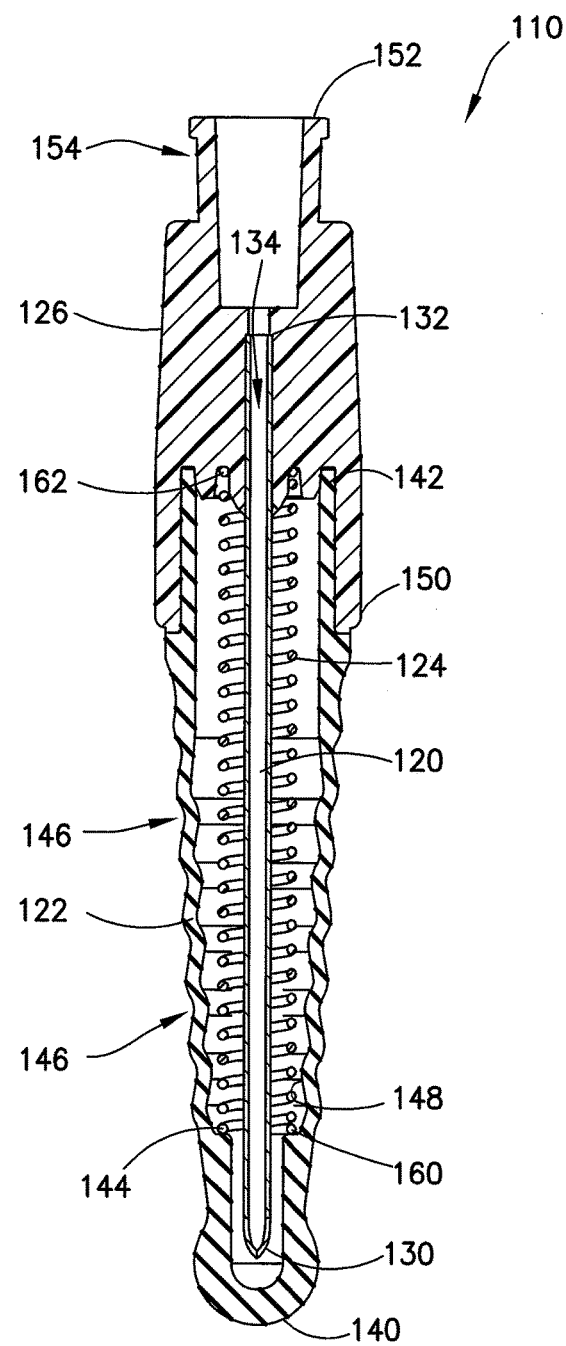
FIG. 10 is a cross-sectional view of a cannula seal assembly in accordance with another embodiment of the present invention.
Figure 11A:
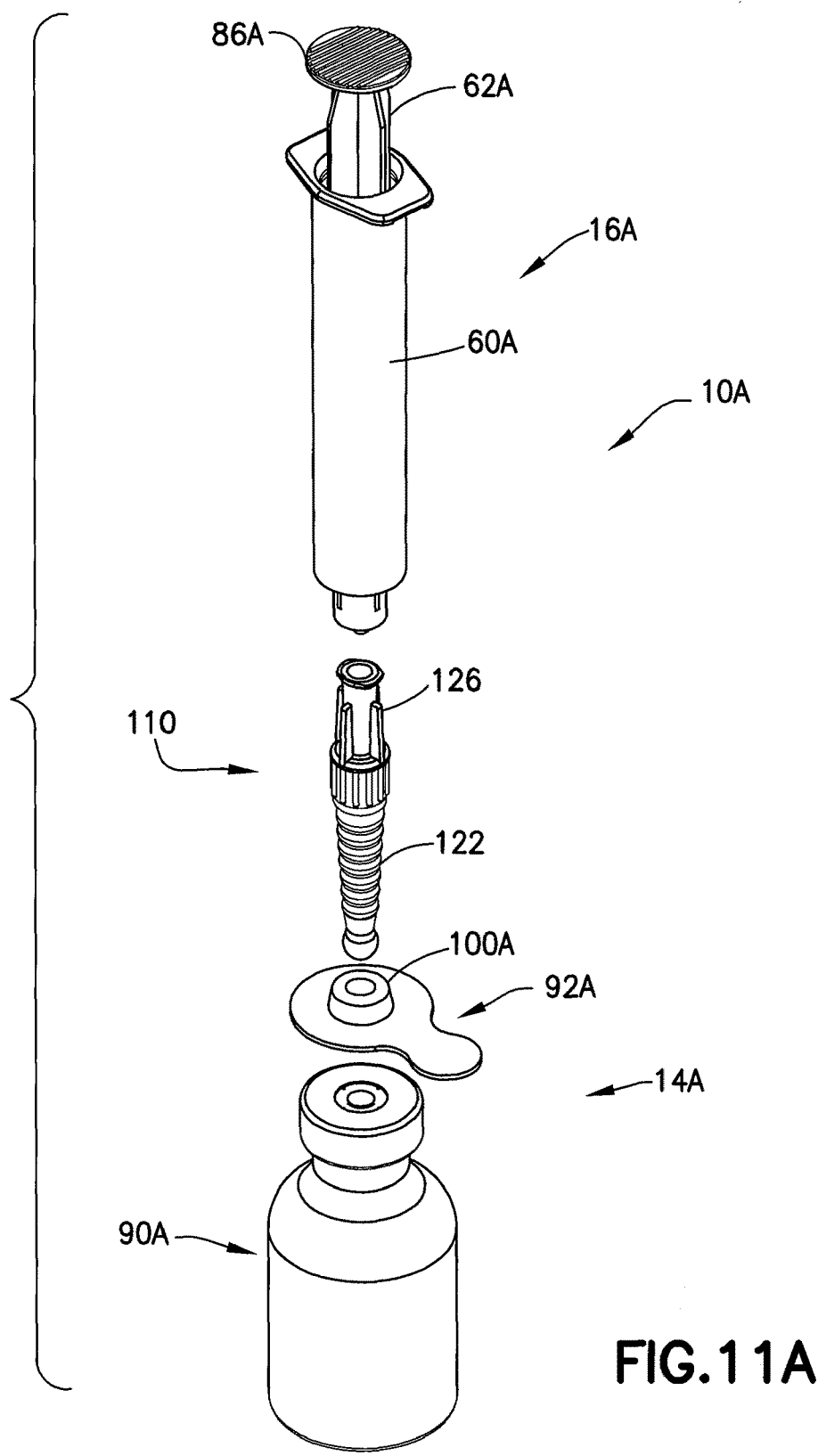
FIG. 11A is an exploded perspective view of a seal system in accordance with another embodiment of the present invention.
Figure 11B:
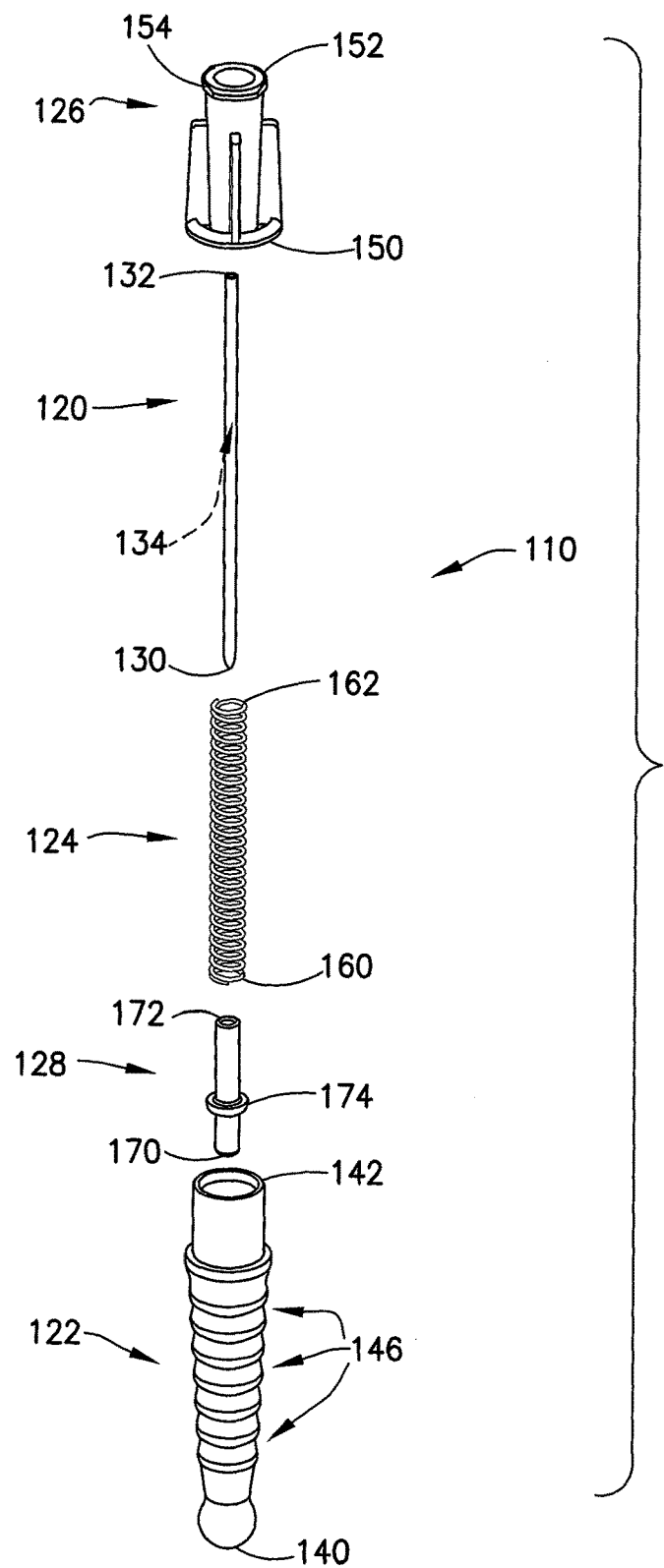
FIG. 11B is an exploded perspective view of a cannula seal assembly in accordance with another embodiment of the present invention.
Figure 12:
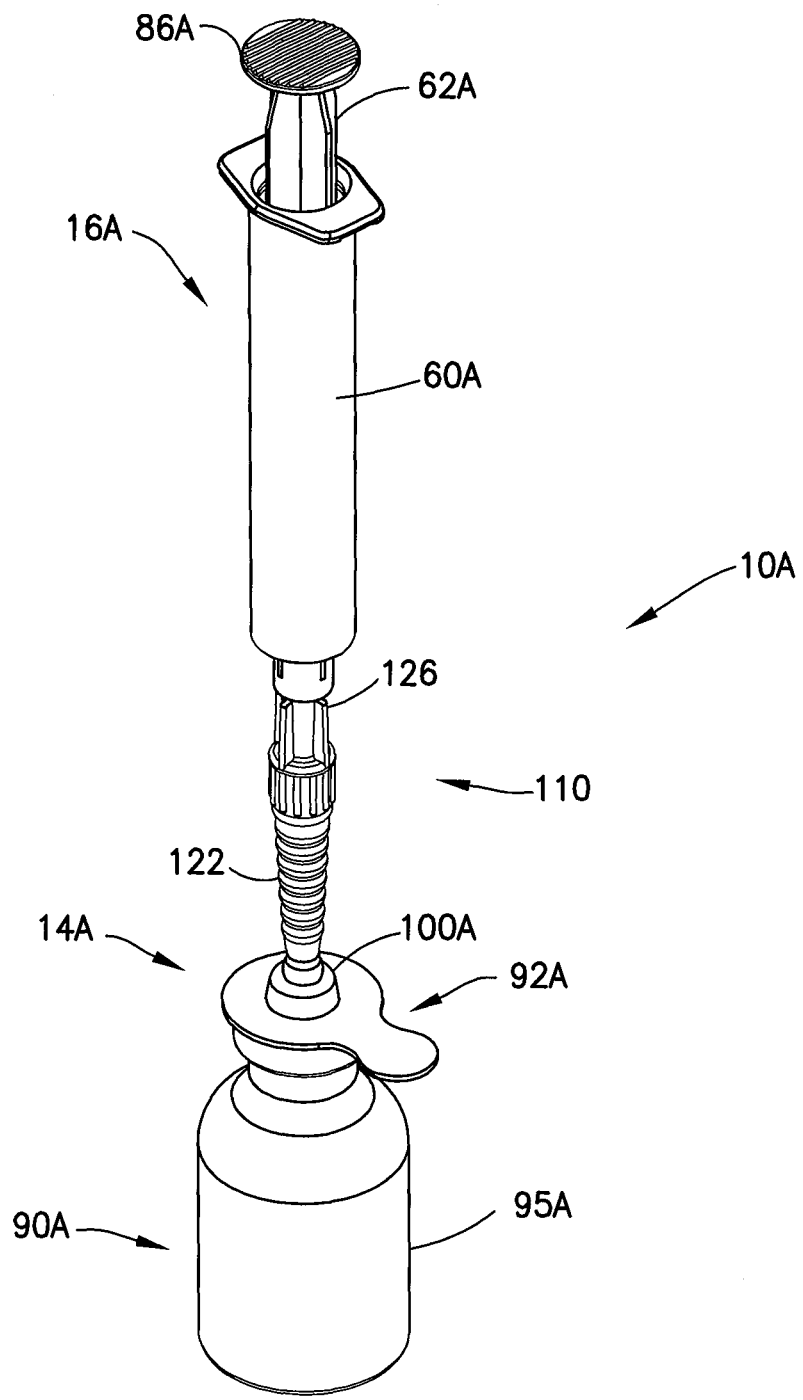
FIG. 12 is an assembled perspective view of the seal system of FIG. 11A in accordance with an embodiment of the present invention.
Figure 13:
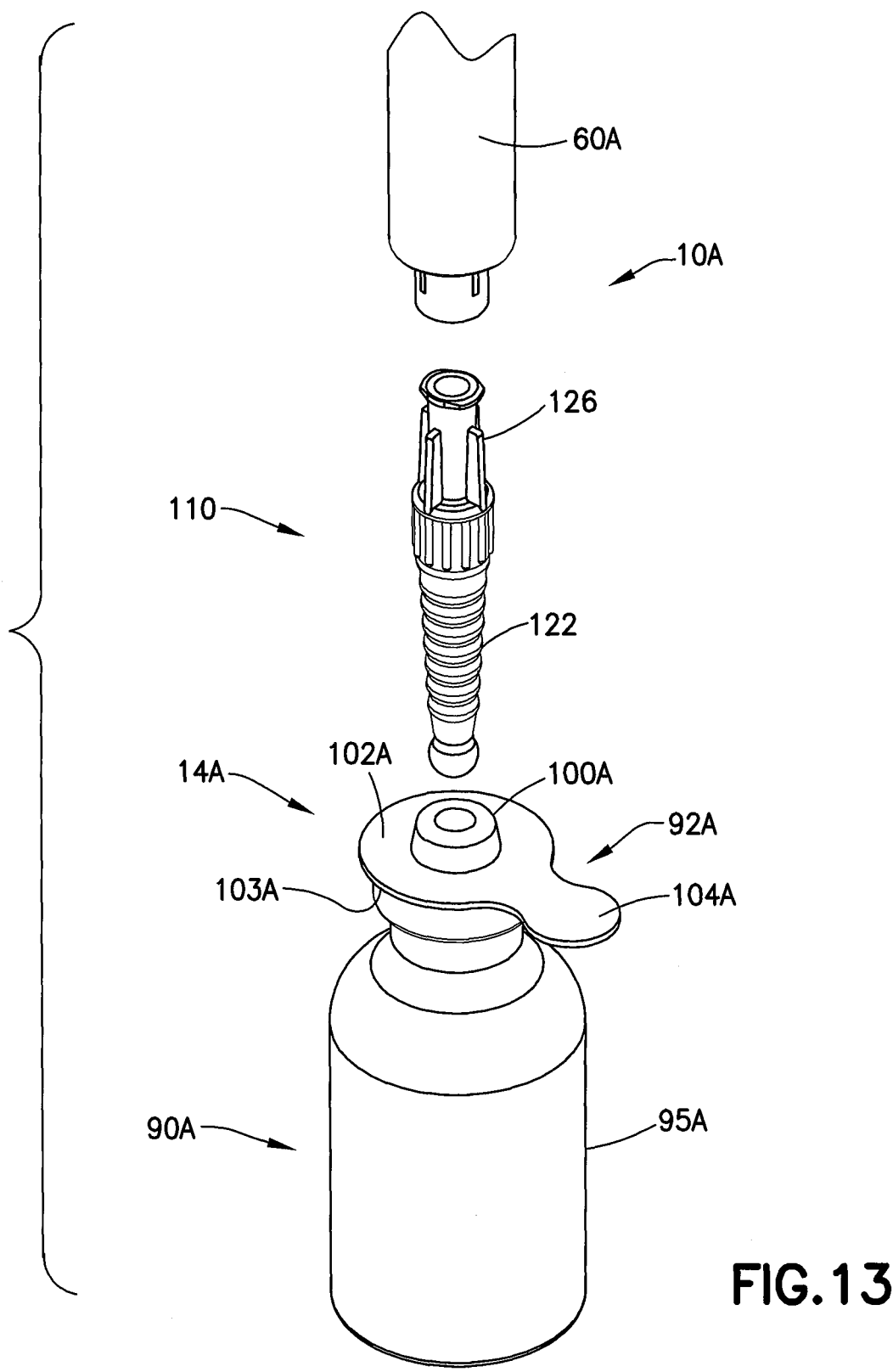
FIG. 13 is a fragmentary, perspective view of the seal system of FIG. 12 with a cannula seal not in communication with a vial seal in accordance with an embodiment of the present invention.

Referring to FIG. 10, spring 124 is disposed over cannula 120 and within cannula seal 122 such that distal end 160 of spring 124 engages shoulder portion 144 of cannula seal 122. In this manner, spring 124 exerts the biasing force on shoulder portion 144 of cannula seal 122. Shoulder portion 144 of cannula seal 122 also ensures that spring 124 is secured between shoulder portion 144 and needle hub 126.

Referring to FIGS. 9-18, needle hub 126 generally includes a distal end 150 and a proximal end 152. Proximal end 152 of needle hub 126 includes a barrel connection portion 154. In one embodiment, barrel connection portion 154 is a threaded portion. Referring to FIGS. 14-18, needle hub 126 supports a portion of cannula 120. Distal end 150 of needle hub 126 also provides a connection with proximal end 162 of spring 124 so that distal end 160 of spring 124 may be compressed relative to proximal end 162 of spring 124 when cannula 120 pierces cannula seal 122 as will be described in more detail below. With spring 124 compressed, spring 124 exerts a biasing force that promotes cannula seal 122 to elastically enclose cannula 120. Referring to FIGS. 14 and 18, in one embodiment, with cannula seal 122 in the sealed position, spring 124 is loaded between shoulder portion 144 of cannula seal 122 and needle hub 126 in a slightly compressed position so that spring 124 exerts a biasing force that retains cannula seal 122 in the sealed position.

Figure 15:
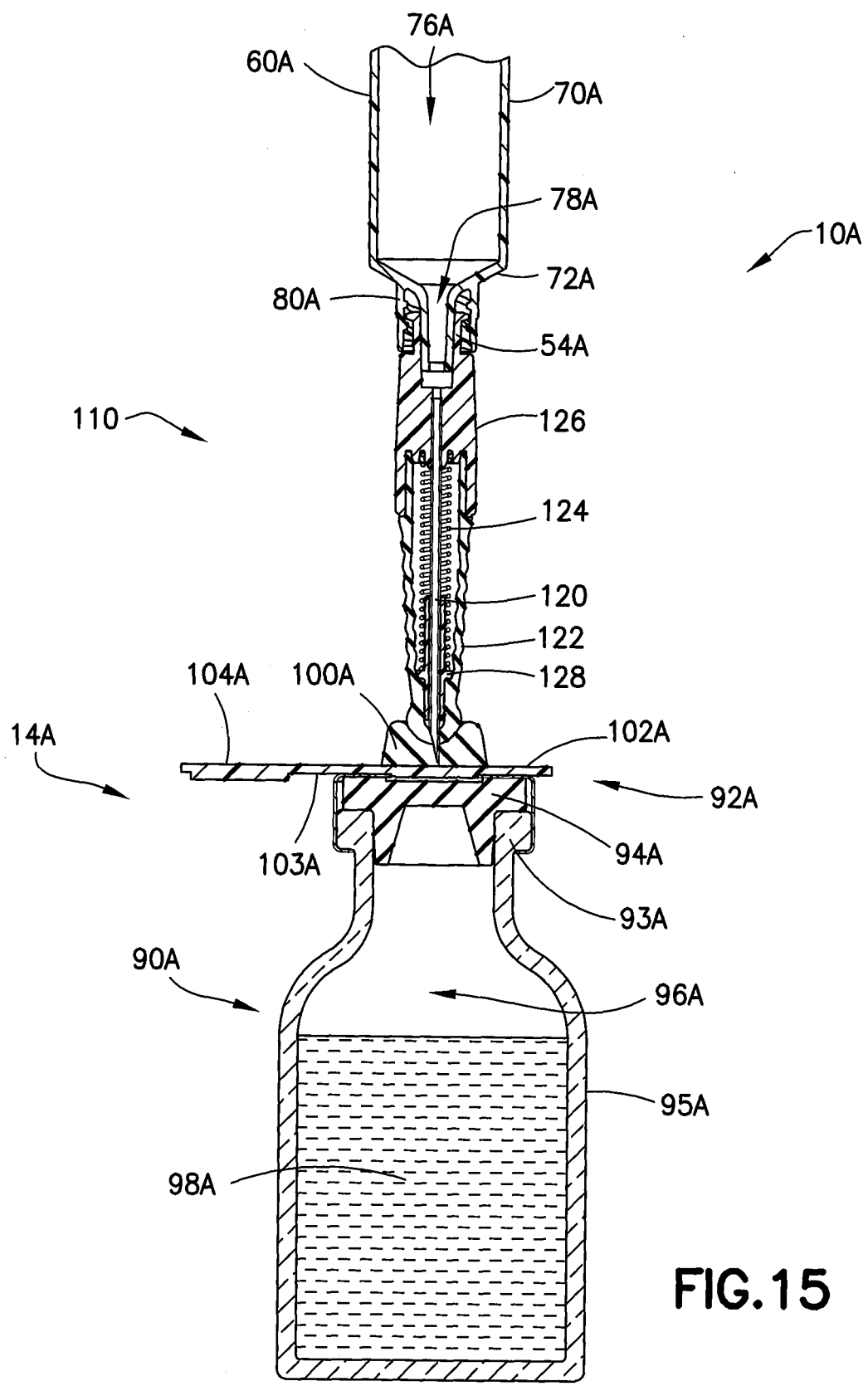
FIG. 15 is a cross-sectional view of the seal system of FIG. 13 with the cannula seal in communication with the vial seal in accordance with an embodiment of the present invention.
Figure 16:
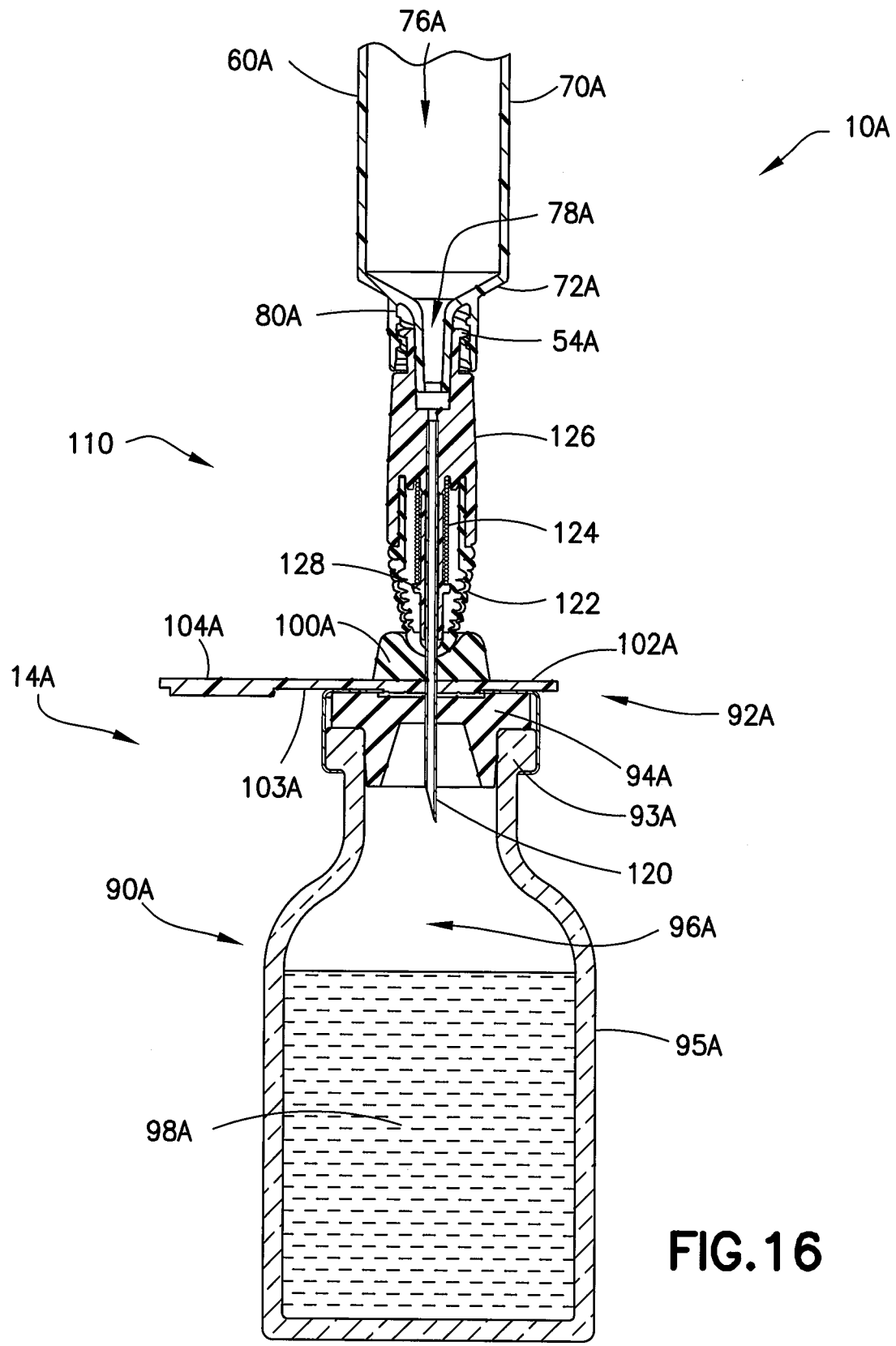
FIG. 16 is a cross-sectional view of the seal system of FIG. 13 with the cannula seal in communication with the vial seal and a cannula piercing the cannula seal, the vial seal, and a vial septum to place a vial chamber in fluid communication with a barrel chamber via the cannula in accordance with an embodiment of the present invention.
Figure 17:
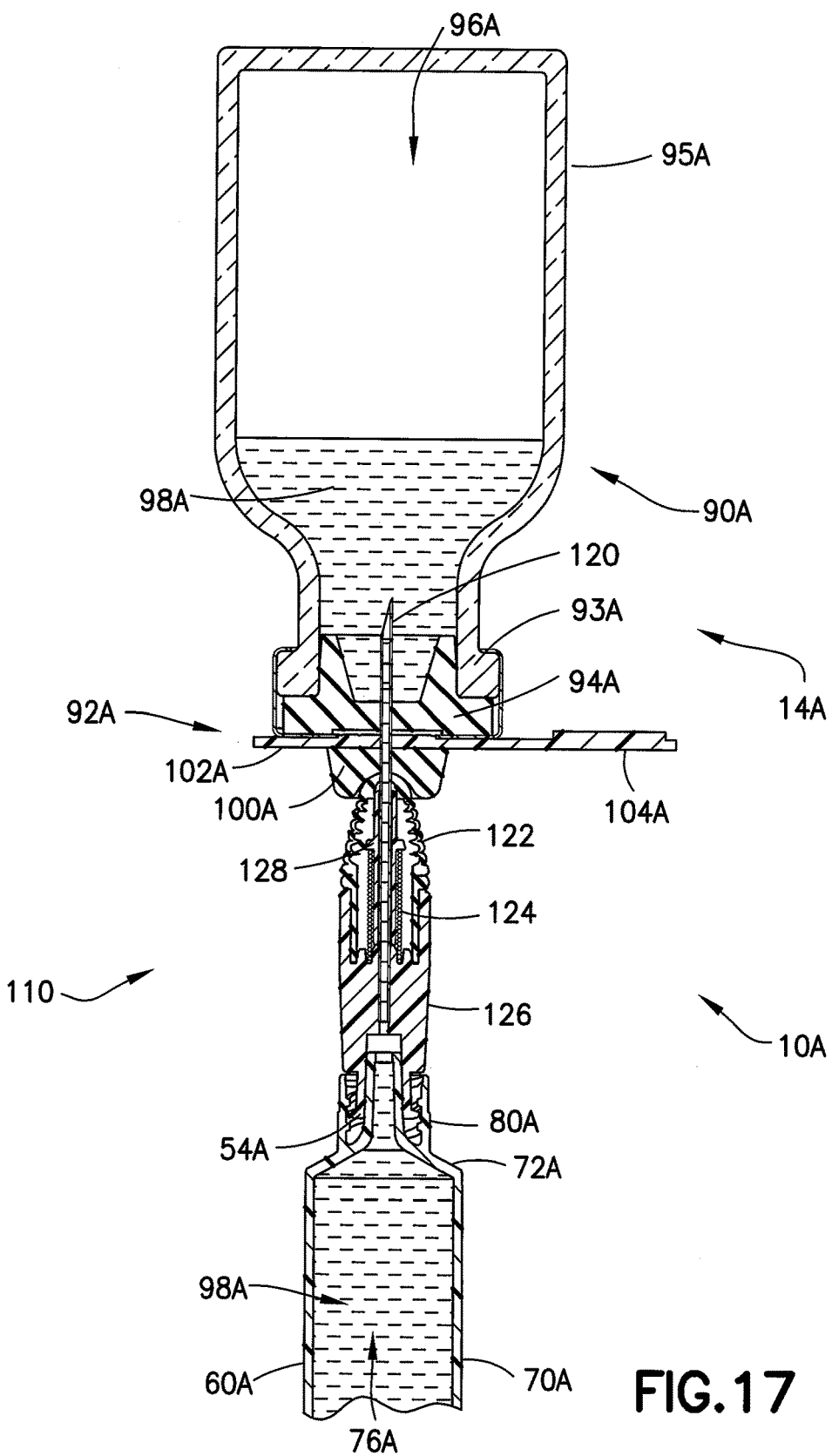
FIG. 17 is a cross-sectional view of the seal system of FIG. 13 with the seal system inverted and the cannula seal in communication with the vial seal and a cannula in fluid communication with a substance contained within a vial chamber in accordance with an embodiment of the present invention.

In one embodiment, referring to FIGS. 9, 10, and 14-18, annular ribbed members 146 of cannula seal 122 provide an additional biasing force that retains cannula seal 122 in the sealed position. Referring to FIGS. 14-16, as cannula 120 is brought into contact with vial seal assembly 14A, annular ribbed members 146 of cannula seal 122 and spring 124 are compressed as cannula 120 pierces cannula seal 122 and vial seal assembly 14A. With annular ribbed members 146 of cannula seal 122 compressed, annular ribbed members 146 exert an additional biasing force that promotes cannula seal 122 to elastically enclose cannula 120.

Referring to FIGS. 11B and 14-18, proximal end 152 of needle hub 126 is attached to barrel 60A of barrel assembly 16A. With needle hub 126 supporting a portion of cannula 120 and with proximal end 152 of needle hub 126 attached to barrel 60A of barrel assembly 16A, needle hub 126 attaches cannula 120 to barrel assembly 16A such that cannula 120 is in fluid communication with a barrel chamber 76A of barrel 60A as will be described in more detail below.

Figure 9:
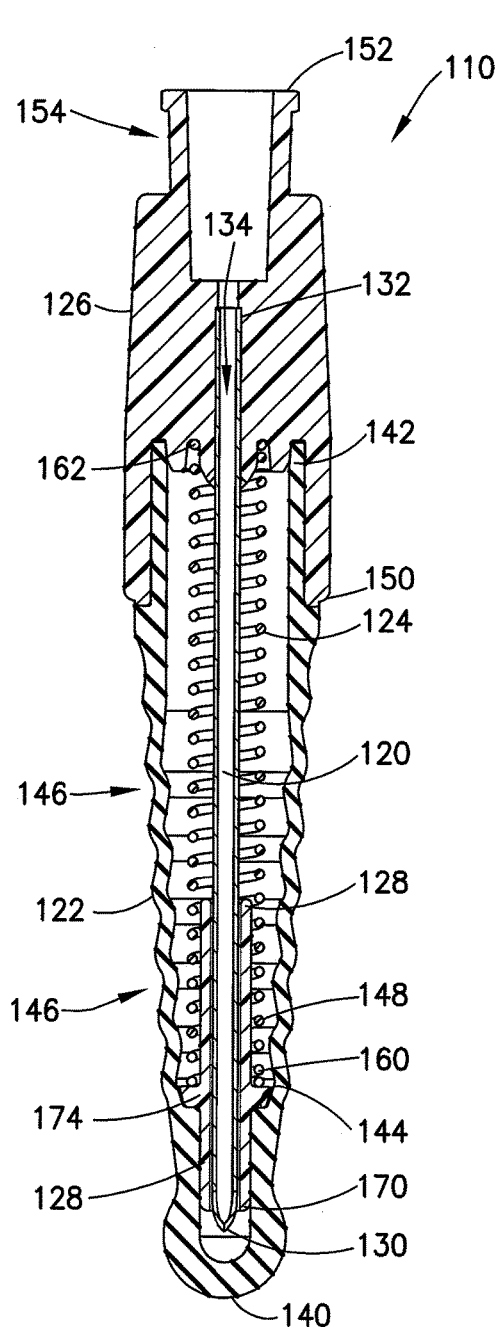
FIG. 9 is a cross-sectional view of a cannula seal assembly with a cannula stabilizing member disposed over a portion of a cannula in accordance with another embodiment of the present invention.

Referring to FIGS. 9-18, in one embodiment, cannula seal assembly 110 includes cannula stabilizing member 128. Referring to FIGS. 9 and 11B, cannula stabilizing member 128 includes a distal end 170, a proximal end 172, and an annular ring 174 therebetween.

Referring to FIG. 9, cannula stabilizing member 128 is disposed within cannula seal 122 such that annular ring 174 of cannula stabilizing member 128 engages shoulder portion 144 of cannula seal 122. In this position, cannula stabilizing member 128 supports a portion of cannula 120 and provides stability to cannula 120 during engagement of cannula 120 with a vial or other device.

With cannula stabilizing member 128 positioned within cannula seal 122, spring 124 is disposed over cannula 120 and within cannula seal 122 such that distal end 160 of spring 124 engages annular ring 174 of cannula stabilizing member 128. In this manner, spring 124 exerts the biasing force on annular ring 174 of cannula stabilizing member 128 which exerts the biasing force on shoulder portion 144 of cannula seal 122.

Referring to FIGS. 4-8 and 14-18, the use of seal system 10, 10A to withdraw a medication such as substance 98, 98A from vial 90, 90A using a barrel 60, 60A such as a syringe will now be described. For the sake of brevity, the components of seal system 10 will be referenced while describing the use of a seal system in accordance with the present disclosure as the components of seal system 10A (FIGS. 9-18) are used in a similar manner as illustrated in FIGS. 14-18.

Initially, referring to FIG. 4, with vial adapter 92 attached to vial 90 such that vial seal 100 is aligned with vial septum 94, a health care provider such as a nurse brings cannula seal assembly 12 in the sealed position to a position adjacent vial seal assembly 14. Next, referring to FIG. 5, with cannula seal 22 in communication with vial seal 100, cannula 20 pierces cannula seal 22 and vial seal 100. Because cannula seal 22 is in communication with vial seal 100, as cannula 20 pierces cannula seal 22, cannula 20 enters vial seal 100. In this manner, cannula 20 is maintained in a leak-proof sealing system throughout the process of engaging cannula 20 with vial 90.

For cannula 20 to pierce cannula seal 22, a force is applied to barrel assembly 16 in a direction generally along arrow A (FIGS. 4 and 14). As cannula 20 is brought into contact with vial seal assembly 14, spring 24 and annular ribbed members 46 of cannula seal 22 are compressed as cannula 20 pierces cannula seal 22 and vial seal 100. Compression of spring 24 creates a spring biasing force that is exerted on cannula seal 22 to elastically enclose cannula 20 simultaneously with cannula 20 exiting vial seal 100 as discussed below. Furthermore, compression of annular ribbed members 46 of cannula seal 22 creates a cannula seal biasing force that is exerted on cannula seal 22 to elastically enclose cannula 20 simultaneously with cannula 20 exiting vial seal 100 as discussed below.

Next, referring to FIG. 6, cannula 20 pierces vial seal 100 and vial septum 94 to place vial chamber 96 in fluid communication with barrel chamber 76 via cannula 20. Referring to FIG. 7, with vial chamber 96 in fluid communication with barrel chamber 76 via cannula 20, seal system 10 is inverted so that substance 98 contained within vial chamber 96 is brought into contact with cannula 20 so that substance 98 may be transferred from vial chamber 96 to barrel chamber 76 via cannula 20.

With seal system 10 in the position shown in FIG. 7, stopper 64 is located adjacent distal end 72 of barrel 60 (as shown in FIG. 1D). When it is desired to aspirate or pull the fluid, such as substance 98, into barrel chamber 76 of barrel 60, a user moves flange portion 86 of plunger rod 62 in a direction generally along arrow B (FIG. 1D) and away from proximal end 74 of barrel 60 until the desired amount of substance 98 is pulled into barrel chamber 76 of barrel 60. In this manner, movement of plunger rod 62 actuates stopper 64 from a position adjacent distal end 72 of barrel 60 (as shown in FIG. 1D) towards a position adjacent proximal end 74 of barrel 60 to withdraw substance 98 from vial chamber 96 to barrel chamber 76 via cannula 20 as shown in FIGS. 7 and 8.

In this manner, movement of stopper 64 in the direction generally along arrow B (FIG. 1D) creates a vacuum inside barrel chamber 76. As the user moves stopper 64, via plunger rod 62 in the direction generally along arrow B, the user actively increases the volume within barrel chamber 76. Because the stopper is sized relative to barrel 60 to provide sealing engagement with the interior wall of barrel 60, as described above, and because cannula 20 locked to distal end 72 of barrel 60 via needle hub 26 is placed in vial 90 containing fluid, no air can enter into barrel chamber 76 and, thus, the same number of air molecules are located within barrel chamber 76 as the user actively increases the volume within barrel chamber 76. This decreases the pressure in barrel chamber 76 relative to the air pressure outside of barrel 60. Therefore, a vacuum, i.e., a space of lower air pressure, is created to pull the fluid, such as substance 98, into barrel chamber 76. Advantageously, barrel assembly 16 can be used to collect a fluid into barrel chamber 76 or to expel a fluid out of barrel chamber 76 as will be described below. Using this technique, the vial chamber 96 is also placed under negative pressure as fluid is withdrawn from the chamber 96. Alternatively, a user may aspirate air into the barrel chamber 76 prior to connection with the cannula seal assembly 12 and inject air into the vial chamber 96 in the same manner as described above to pressurize the vial chamber 96. Upon withdrawing the fluid, such as substance 98, from the vial chamber 96, the vial chamber 96 will return to a neutral or atmospheric pressure. Accordingly, the volume of air aspirated into the barrel chamber 76 for injection into the vial chamber 96 preferably corresponds to the volume fluid intended to be removed from the vial chamber 96.

With the desired amount of substance 98 pulled into barrel chamber 76 of barrel 60, a user may now disengage cannula 20 from vial 90 as shown in FIG. 8. Seal system 10, 10A of the present disclosure allows a user to disengage cannula 20 from vial 90 maintaining a leak-proof sealing. As discussed above, as cannula 20 is brought into contact with vial seal assembly 14, spring 24 and annular ribbed members 46 of cannula seal 22 are compressed as cannula 20 pierces cannula seal 22, vial seal 100, and vial septum 94. Compression of spring 24 creates a spring biasing force that is exerted on cannula seal 22 and compression of annular ribbed members 46 of cannula seal 22 creates a cannula seal biasing force that is exerted on cannula seal 22. Because cannula seal 22 is in communication with vial seal 100 throughout a process of transferring substance 98 from vial chamber 96 to barrel chamber 76 via cannula 20, as cannula 20 is removed from vial 90 and vial seal 100, the spring biasing force of spring 24 and the cannula seal biasing force of annular ribbed members 46 of cannula seal 22 are exerted on cannula seal 22 to elastically enclose cannula 20 simultaneously with cannula 20 exiting vial seal 100. Advantageously, seal system 10 maintains a leak-proof seal enclosing cannula 20 at all times during engagement of cannula 20 with vial 90, during transfer of the substance 98 from vial chamber 96 to barrel chamber 76 via cannula 20, and during disengagement of cannula 20 from vial 90 to substantially prevent leakage of liquid or air from the system 10.

As discussed above, seal system 10, 10A is also compatible with a drug reconstitution system. Certain drugs are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. In addition, drugs may be provided as multipart systems which require mixing prior to administration. For example, one or more liquid components, such as flowable slurries, and one or more dry components, such as powdered or granular components, may be provided in separate containers which require mixing prior to administration.

In one embodiment, barrel 60 contains a first substance or flowable substance (e.g., slurry or liquid) such as a diluent, and vial 90 contains a second substance, such as a powdered or granular substance intended for reconstitution. For example, barrel chamber 76 of barrel 60 may be adapted to contain a flowable material, such as a liquid diluent or other substance intended for drug reconstitution therein. The flowable material may be a liquid or slurry component of a drug or medicament. It is further understood that the flowable material may include one or more constituent elements (e.g., two different types of drug components) containing one or more pharmacologically active agents. Alternatively, the flowable material may serve solely as a diluent for a dry drug and contain no pharmacologically active elements.

In one embodiment, barrel chamber 76 of barrel 60 may be pre-filled with the liquid diluent or other substance intended for drug reconstitution. In this manner, barrel 60 can be manufactured, pre-filled with a diluent, sterilized, and packaged in appropriate packaging for delivery, storage, and use by the end user.

Vial 90 contains the second component of the drug to be reconstituted. The second drug component may be provided in powdered or granular form (e.g., a lyophilized powder). Alternatively, the second component is provided in a wet form, such as a liquid or slurry, for combination with the flowable material in barrel 60.

Referring to FIGS. 4-8 and 14-18, the use of seal system 10, 10A to reconstitute a first substance or liquid contained within barrel chamber 76 of barrel 60 with a second substance or powder contained within vial 90 will now be described. For the sake of brevity, the components of seal system 10 will be referenced while describing the use of a seal system in accordance with the present disclosure with a drug reconstitution system as the components of seal system 10A (FIGS. 9-18) are used in a similar manner as illustrated in FIGS. 14-18.

Initially, referring to FIG. 4, with vial adapter 92 attached to vial 90 such that vial seal 100 is aligned with vial septum 94, a health care provider such as a nurse brings cannula seal assembly 12 in the sealed position to a position adjacent vial seal assembly 14. Next, referring to FIG. 5, with cannula seal 22 in communication with vial seal 100, cannula 20 pierces cannula seal 22 and vial seal 100. Because cannula seal 22 is in communication with vial seal 100, as cannula 20 pierces cannula seal 22, cannula 20 enters vial seal 100. In this manner, cannula 20 is maintained in a leak-proof sealing system throughout the process of engaging cannula 20 with vial 90.

For cannula 20 to pierce cannula seal 22, a force is applied to barrel assembly 16 in a direction generally along arrow A (FIGS. 4 and 14). As cannula 20 is brought into contact with vial seal assembly 14, spring 24 and annular ribbed members 46 of cannula seal 22 are compressed as cannula 20 pierces cannula seal 22 and vial seal 100. Compression of spring 24 creates a spring biasing force that is exerted on cannula seal 22 to elastically enclose cannula 20 simultaneously with cannula 20 exiting vial seal 100 as discussed below. Furthermore, compression of annular ribbed members 46 of cannula seal 22 creates a cannula seal biasing force that is exerted on cannula seal 22 to elastically enclose cannula 20 simultaneously with cannula 20 exiting vial seal 100 as discussed above.

Next, referring to FIG. 6, cannula 20 pierces vial seal 100 and vial septum 94 to place vial chamber 96 in fluid communication with barrel chamber 76 via cannula 20. At this point, the user presses down on plunger rod 62 in a direction generally along arrow C (FIG. 1D) advancing stopper 64 within barrel 60 from a position adjacent proximal end 74 of barrel 60 towards a position adjacent distal end 72 of barrel 60 to expel the liquid from barrel chamber 76 of barrel 60 and into vial 90 via cannula 20. Once the liquid is entirely injected into vial 90, the user may shake vial 90 to mix the dry and liquid components of the drug. In some embodiments, mixing may be accomplished in a matter of seconds whereas in other embodiments mixing can take as long as 20 minutes. The user can tell that all fluid has been expelled from barrel 60 when stopper 64 is at the base of barrel 60 and plunger rod 62 cannot be further advanced. The amount of mixing required is based on the composition, solubility, and viscosity of the dry and liquid components initially present in vial 90 and barrel 60 to be reconstituted.

Referring to FIG. 7, after the dry and liquid components are reconstituted in vial 90 and with vial chamber 96 in fluid communication with barrel chamber 76 via cannula 20, seal system 10 is inverted so that the reconstituted substance 98 contained within vial chamber 96 is brought into contact with cannula 20 so that reconstituted substance 98 may be transferred from vial chamber 96 to barrel chamber 76 via cannula 20.

With seal system 10 in the position shown in FIG. 7, stopper 64 is located adjacent distal end 72 of barrel 60 (as shown in FIG. 1D). When it is desired to aspirate or pull the reconstituted substance 98 into barrel chamber 76 of barrel 60, a user moves flange portion 86 of plunger rod 62 in a direction generally along arrow B (FIG. 1D) and away from proximal end 74 of barrel 60 until the desired amount of reconstituted substance 98 is pulled into barrel chamber 76 of barrel 60. In this manner, movement of plunger rod 62 actuates stopper 64 from a position adjacent distal end 72 of barrel 60 (as shown in FIG. 1D) towards a position adjacent proximal end 74 of barrel 60 to withdraw reconstituted substance 98 from vial chamber 96 to barrel chamber 76 via cannula 20 as shown in FIGS. 7 and 8.

With the desired amount of reconstituted substance 98 pulled into barrel chamber 76 of barrel 60, a user may now disengage cannula 20 from vial 90 as shown in FIG. 8. Seal system 10, 10A of the present disclosure allows a user to disengage cannula 20 from vial 90 maintaining a leak-proof sealing. As discussed above, as cannula 20 is brought into contact with vial seal assembly 14, spring 24 and annular ribbed members 46 of cannula seal 22 are compressed as cannula 20 pierces cannula seal 22, vial seal 100, and vial septum 94. Compression of spring 24 creates a spring biasing force that is exerted on cannula seal 22 and compression of annular ribbed members 46 of cannula seal 22 creates a cannula seal biasing force that is exerted on cannula seal 22. Because cannula seal 22 is in communication with vial seal 100 throughout a process of transferring substance 98 from vial chamber 96 to barrel chamber 76 via cannula 20, as cannula 20 is removed from vial 90 and vial seal 100, the spring biasing force of spring 24 and the cannula seal biasing force of annular ribbed members 46 of cannula seal 22 are exerted on cannula seal 22 to elastically enclose cannula 20 simultaneously with cannula 20 exiting vial seal 100. Advantageously, seal system 10 maintains a leak-proof seal enclosing cannula 20 at all times during engagement of cannula 20 with vial 90, during transfer of the substance 98 from vial chamber 96 to barrel chamber 76 via cannula 20, and during disengagement of cannula 20 from vial 90 to substantially prevent leakage of liquid or air from the system 10.

Figure 19:
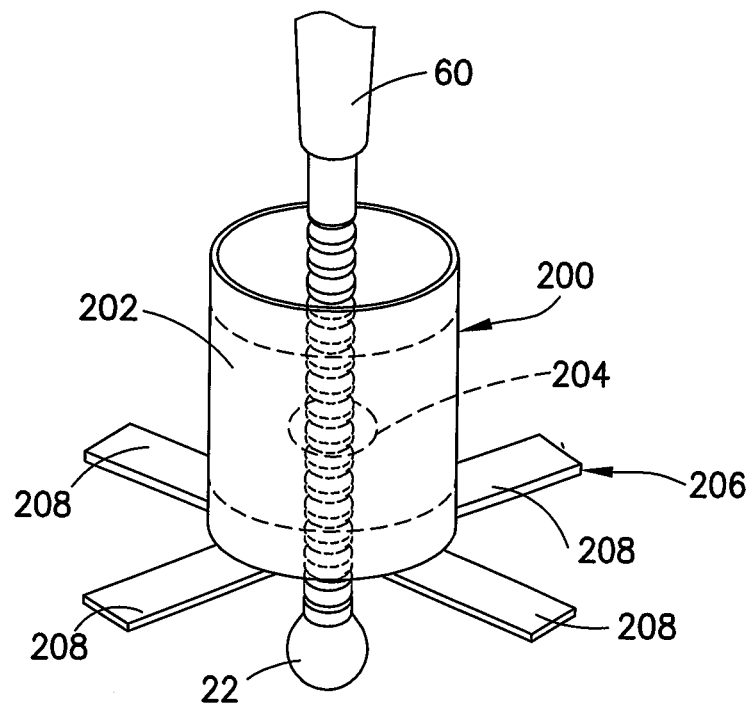
FIG. 19 is a perspective view of an alignment mechanism according to one embodiment of the present invention.

Referring to FIG. 19, the seal systems 10, 10A described above and shown in FIGS. 1-18 may be utilized with an alignment mechanism 200. The alignment mechanism 200 will be described with reference to seal system 10 shown in FIGS. 1-8 and will operate in the same manner in connection with the seal system 10A shown in FIGS. 9-18. The alignment mechanism may be provided to reduce misaligned contact between the cannula seal 22 and the vial seal 100 to further ensure sealing contact between the cannula seal 22 and the vial seal 100. In one embodiment, the alignment mechanism 200 includes a body 202 having a guide 204, such as an opening, and an attachment arrangement 206. The attachment arrangement secures the alignment mechanism 200 to the vial 90. In one embodiment, as shown in FIG. 19, the attachment arrangement 206 includes a plurality of extensions 208 that may adhere or grip the vial 90. The attachment arrangement 206, however, may be any suitable arrangement for securing the alignment mechanism 200 to the vial 90, such as clips, snap-fit arrangement, etc. The guide 204 of the alignment mechanism receives the cannula seal 22 to ensure that the cannula seal 22 has an orientation to ensure a proper seal between the cannula seal 22 and the vial seal 100. In particular, the guide 204 may be embodied as an opening 210 extending the entire or part of the length of the body 202 that is sized and shaped to limit the angle of the cannula seal 22 relative to the vial seal 100. The vial seal 100 may be formed integrally with the alignment mechanism 200 or may be formed separately.

Figure 22:
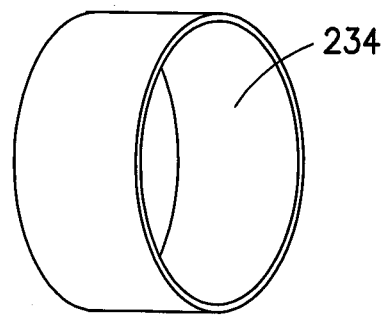
FIG. 22 is a perspective view of a filter utilized in the seal system of FIG. 20 according to one embodiment of the present invention.
Figure 20:
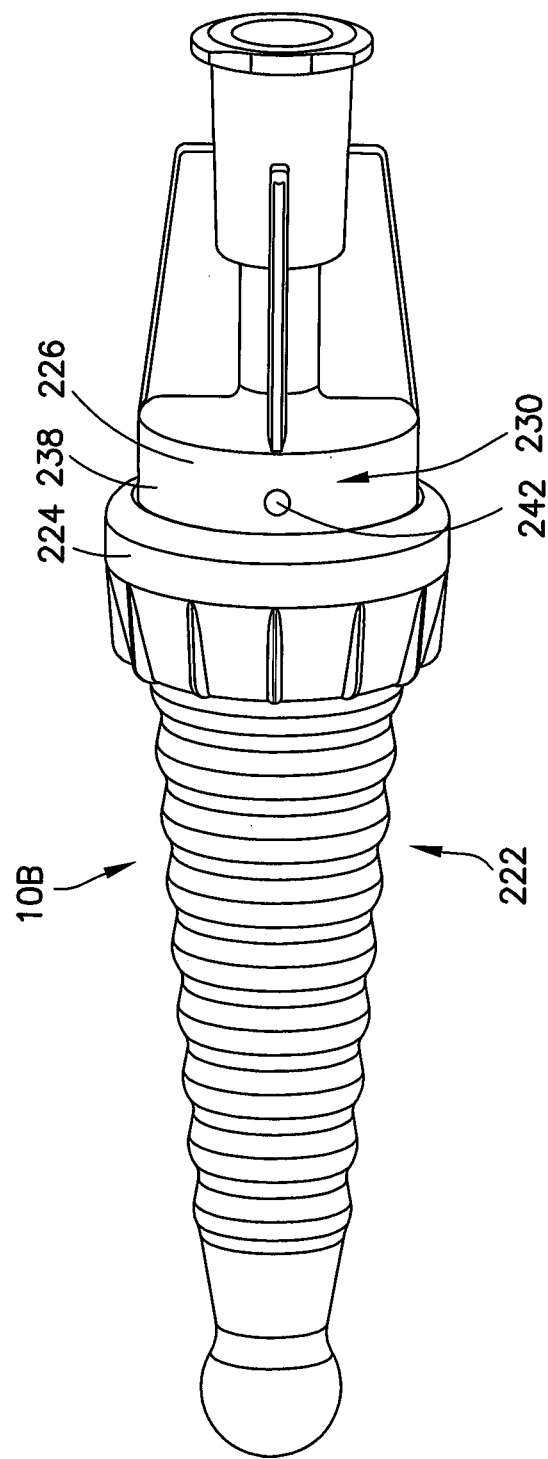
FIG. 20 is a perspective view of a seal system according to a further embodiment of the present invention.
Figure 21:
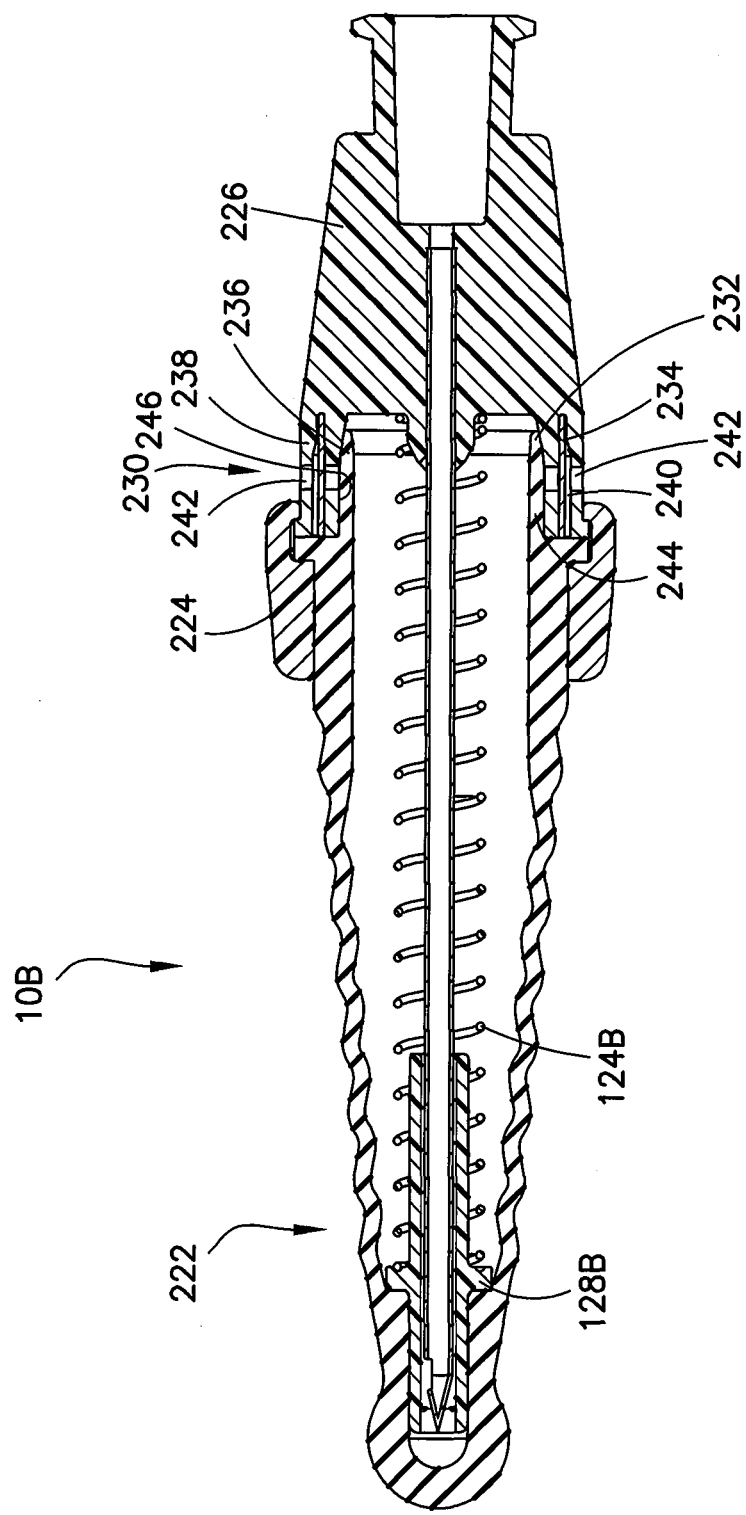
FIG. 21 is a cross-sectional view of the seal system of FIG. 20 according to one embodiment of the present invention.

FIGS. 20-22 illustrate a further exemplary embodiment of the present disclosure. The embodiment illustrated in FIGS. 20-22 includes, similar components to the embodiments illustrated in FIGS. 1-18, and the similar components are denoted by a reference number followed by the letter B. For the sake of brevity, these similar components and the similar steps of using seal system 10B (FIGS. 20-22) will not all be discussed in conjunction with the embodiment illustrated in FIGS. 20-22.

Referring to FIGS. 20-22, seal system 10B includes a cannula 120B, a cannula stabilizing member 128B, a spring 124B, a cannula seal assembly 222, a locking ring 224, and a needle hub 226. The cannula seal assembly 222 and needle hub 226 are similar to the cannula seal 122 and needle hub 126 described above in connection with seal system 10B shown in FIGS. 9-18. The seal system 10B, however, is configured to provide an aspiration arrangement to allow air to enter the seal system 10B for aspirating air into a syringe barrel while using the system 10B. In particular, the aspiration arrangement allows a user to aspirate air into the barrel chamber 76 after the seal system 10B is secured to the barrel assembly 16. In one embodiment, the aspiration arrangement 230 includes a one-way valve 232 and filter 234. As shown in FIG. 21, the needle hub 226 includes an inner wall 236 and an outer wall 238 that defines an annular recess 240. The needle hub 226 further defines at least one passageway 242 that extends perpendicularly to a longitudinal axis of the hub 226. Although one or more passageways 242 may be provided, the needle hub 226, as shown in FIG. 21, defines two passageways 242 positioned opposite from each other relative to a circumference of the hub 226. The passageways 242 each extend through the outer wall 238, the annular recess 240, and through the inner wall 236. In one embodiment, as shown in FIG. 22, the filter 234 is generally ring-shaped or a flat filter sheet that is bent into a ring-shape and is positioned within the annular recess 240, although other suitable arrangements may be utilized. The filter 234 may be any suitable commercially available filter, such as a particulate air filter having a pore size of 0.2 µm or larger. The filter 234 may be configured remove viable micro-organisms.

Referring again to FIG. 21, in one embodiment, the one-way valve 232 is embodied as an extension 244 of the cannula seal assembly 222 that extends into the needle hub 228. The extension 244 is formed integrally with the cannula seal assembly 222, although the extension 244 may be formed separately. The extension 244 of the cannula seal assembly 222 abuts and extends along at least a portion of an inner surface 246 of the inner wall 236. The extension 244 is configured to selectively allow the flow of outside air through the passageways 242 and the filter 234 and into the cannula seal assembly 222. In particular, in response to a pressure drop within the cannula seal assembly 222 caused by aspiration, the extension 244 will deflect inwardly to open the passageways 242 and allow outside air to be drawn into the barrel chamber 76. After aspiration, the extension 244 will return to its original position to block or close the passageways 242. When the cannula seal assembly 222 is under a positive pressure, the extension 244 is forced radially outward and continues to block and seal the passageways 242. As discussed above, air may first be injected into the vial chamber 96 prior to withdrawing fluid, such as substance 98, from the vial chamber 96. Accordingly, the one-way valve 232 and filter 234 allows a user to aspirate air into the barrel chamber 76 after the seal system 10B is secured to the barrel assembly 16. Furthermore, the filter 234 is configured to filter the outside air that is aspirated into the barrel assembly 16, which advantageously allows clean filter air to be injected into the vial chamber 96.

Referring to FIGS. 20 and 21, in one embodiment, the locking ring 224 is generally ring-shaped and is configured to secure the cannula seal assembly 222 to the needle hub 226. In particular, the locking ring 224 has a snap-fit engagement with the cannula seal assembly 222 and the needle hub 226, although other suitable arrangements for securing the locking ring 224 may be utilized. Although not shown, the locking ring 224 may extend the length of the needle hub 226 and may be positioned adjacent to the luer connection and include an arrangement to substantially prevent the unintended disconnection of the barrel assembly 16 from the cannula seal assembly 222.

Furthermore, although not shown, the seal systems 10, 10A, 10B described above and shown in FIGS. 1-22 may include a shielding arrangement or safety-lock mechanism to prevent unintended exposure of the cannula 20. The shielding arrangement may include a pivoting shielding member that is hinged to the needle hub or other suitable area to selectively shield the distal end 30 of the cannula 20. The shielding arrangement may also include a cylinder or shielding member that is biased toward the distal end 30 of the cannula 20 to prevent movement of the seal systems 10, 10A, 10B. Any other suitable shielding or safety-lock mechanism may be utilized to prevent the unintended exposure of the cannula 20.

While this disclosure has been described as having exemplary designs, the present disclosure can be further modified within the spirit and scope of this disclosure. This application is therefore intended to cover any variations, uses, or adaptations of the disclosure using its general principles.

Further, this application is intended to cover such departures from the present disclosure as come within known or customary practice in the art to which this disclosure pertains and which fall within the limits of the appended claims.

What is claimed is:

1. A system comprising:
  a needle hub having a proximal end and a distal end, the proximal end of the needle hub having a connection portion configured to receive a first container;
  a cannula received by the needle hub, the cannula having a proximal end and a distal end and a lumen;
  a cannula seal comprising a resilient sleeve enclosing at least a portion of the cannula, the cannula seal having an open proximal end and a distal end, the distal end of the cannula seal including a tip having a vial engagement portion, wherein the needle hub and cannula seal define a collapsible capsule having an interior cavity;
  a vial adapter configured to be attached to a second container, the vial adapter having a vial seal and a body, the vial seal is configured to engage the cannula seal, the body of the vial adapter is configured to engage a septum of the second container; and
  an aspiration arrangement having a filter disposed in the collapsible capsule, the filter disposed between the interior cavity and an exterior of the collapsible capsule thereby allowing air to be aspirated through the filter and into the cannula lumen,
  wherein the cannula seal has a first position where the cannula seal encloses the distal end of the cannula and a second position where the cannula seal is engaged to the vial and is retracted to insert the distal end of the cannula and lumen to an interior of the vial, and further wherein the vial seal of the vial adapter defines a tip recess that is configured to receive the vial engagement portion of the distal end of the cannula seal.

2. The system of claim 1, further comprising a vial defining a vial chamber, a first substance contained within the vial chamber, the vial including a vial septum engaged with the vial to seal the first substance within the vial chamber, the body of the vial adapter configured to be attached to the vial septum of the vial.

3. The system of claim 2, wherein with the vial adapter attached to the vial such that the vial seal is aligned with the vial septum and with the cannula seal in communication with the vial seal, the cannula is configured to pierce the cannula seal, the vial seal, and the vial septum to place the vial chamber in fluid communication with a barrel chamber via the cannula, and when the cannula is removed from the vial, as the cannula is withdrawn from the vial seal, the cannula seal elastically encloses the cannula simultaneously with the cannula exiting the vial seal.

4. The system of claim 2, further comprising a syringe barrel defining a barrel chamber, the connection portion of the needle hub configured to receive the syringe barrel.

5. The system of claim 4, wherein with the vial chamber is in fluid communication with the barrel chamber, the first substance is capable of being transferred from the vial chamber to the barrel chamber via the cannula.

6. The system of claim 1, further comprising a spring disposed over the cannula seal such that the cannula seal is positioned between the cannula and the spring, wherein the spring biases the cannula seal to the first position.

7. The system of claim 1, further comprising a spring disposed over the cannula such that the spring is positioned between the cannula and the cannula seal, wherein the spring biases the cannula seal to the first position.

8. The system of claim 7, further comprising a cannula stabilizing member disposed over a portion of the cannula, the cannula stabilizing member enclosed within the cannula seal.

9. The system of claim 1, wherein when the cannula seal is in the first position, the cannula seal extends from the needle hub to a position beyond the distal end of the cannula.

10. The system of claim 1, wherein the vial seal comprises a resilient seal.

11. The system of claim 1, wherein the filter radially encircles at least a portion of the collapsible capsule.

12. The system of claim 11, wherein the aspiration arrangement further comprises a one-way valve.

13. The system of claim 12, wherein the needle hub includes an inner wall and an outer wall to define an annular recess, the needle hub defining a passageway extending through the outer wall and the inner wall, the filter is positioned within the annular recess, the one-way valve comprising an extension of the cannula seal that extends into the needle hub.

14. The system of claim 12, wherein the one way valve comprises at least one orifice in the collapsible capsule and at least a portion of the resilient sleeve is adapted to form a flapper covering the at least one orifice.

15. The system of claim 1, wherein the cannula seal includes a plurality of annular rib members.

16. The system of claim 15, further comprising a spring that is configured to bias the cannula seal towards the first position.

17. The system of claim 1, wherein the vial adapter comprises a body having an adhesive configured to secure the vial adapter to the second container.

18. The system of claim 1, wherein the cannula seal is a unitary device.

19. The system of claim 1, wherein the collapsible capsule is a unitary device.

20. A method of transferring fluids between first and second containers, the method comprising:
  providing a needle hub, a cannula received by the needle hub, and a cannula seal enclosing at least a portion of the cannula, the cannula seal having a first position where the cannula seal encloses a distal end of the cannula and a second position where the distal end of the cannula is positioned outside of the cannula seal, the cannula seal having an open proximal end and a distal end, the distal end of the cannula seal including a tip having a vial engagement portion, wherein the needle hub and cannula seal define a collapsible capsule having an interior cavity;
  securing the needle hub to the first container;
  attaching a vial adapter to the second container, the vial adapter having a vial seal and a body, the vial seal being configured to engage the cannula seal, the body of the vial adapter being configured to engage a septum of the second container;
  engaging the vial seal of the vial adapter with the cannula seal via a tip recess on the vial adapter that is configured to receive the vial engagement portion of the distal end of the cannula seal, and piercing the cannula seal and the vial seal with the cannula such that the cannula is in fluid communication with the second container, the cannula seal moving from the first position to the second position;
  aspirating the first container after securing the needle hub to the first container through a filter disposed in the collapsible capsule said filter disposed between said interior cavity and an exterior of the collapsible capsule;

transferring fluid from the second container to the first container; and withdrawing the cannula from the second container and disengaging the cannula seal from the vial seal of the vial adapter with the cannula seal returning to the first position.

21. The method of claim 20, wherein the aspiration occurs through a one-way valve.

22. The method of claim 21, further comprising deflecting at least a portion of a resilient sleeve in the operation of the one way valve.

* * * * *